United States Patent
Kim et al.

(10) Patent No.: US 7,728,194 B2
(45) Date of Patent: Jun. 1, 2010

(54) DNA FRAGMENT SPECIFIC TO CYTOPLASMIC MALE STERILE PEPPER AND USE THEREOF

(75) Inventors: Byung-Dong Kim, Gyeonggi-do (KR); Dong-Hwan Kim, Gyeonggi-do (KR); Jeong-Gu Kang, Kwangju (KR)

(73) Assignee: Seoul National University Industry Foundation, Seoul (KR)

( * ) Notice: Subject to any disclaimer, the term of this patent is extended or adjusted under 35 U.S.C. 154(b) by 822 days.

(21) Appl. No.: 10/555,824

(22) PCT Filed: May 7, 2004

(86) PCT No.: PCT/KR2004/001063
§ 371 (c)(1), (2), (4) Date: Nov. 28, 2006

(87) PCT Pub. No.: WO2004/099416
PCT Pub. Date: Nov. 18, 2004

(65) Prior Publication Data
US 2007/0180582 A1    Aug. 2, 2007

(30) Foreign Application Priority Data
May 7, 2003    (WO) .............. PCT/KR2003/000904
May 9, 2003    (KR) ..................... 10-2003-0029269

(51) Int. Cl.
C12N 15/29 (2006.01)
C12N 15/62 (2006.01)
C12N 15/82 (2006.01)
A01H 1/02 (2006.01)
A01H 5/00 (2006.01)

(52) U.S. Cl. ................. 800/303; 800/278; 800/288; 800/306; 800/317.1; 800/317.3; 800/317.4; 435/69.8; 536/23.6

(58) Field of Classification Search .................. None
See application file for complete search history.

(56) References Cited

U.S. PATENT DOCUMENTS 6,479,735 B1 * 11/2002 Araya et al. ................. 800/303

OTHER PUBLICATIONS

Kim et al. Journal of the Korean Society for Horticultural Science 42(2): 121-127 (2001).*
Araya et al. Accession No. AR254351, SEQ ID No:5 of US 6,479,735 (2002).*

* cited by examiner

*Primary Examiner*—David T Fox
(74) *Attorney, Agent, or Firm*—Alston & Bird LLP

(57) ABSTRACT

The present invention relates to a DNA fragment specific to a cytoplasmic male sterile pepper comprising a polynucleotide of SEQ ID NO: 1, a candidate polynucleotide (named orf456) associated with cytoplasmic male sterile pepper consisting of a $223^{rd}$ to $678^{th}$ nucleic acid of SEQ ID NO:1, and a polynucleotide of SEQ ID NO: 2. The DNA fragment specific to cytoplasmic male sterile pepper comprising a polynucleotide of SEQ ID NOs: 1 or 2 can be used for identifying cytoplasmic type between male sterile and male fertile pepper by the PCR method. In addition, hybrid pepper breeders/seed companies could detect impurities of the maintainer line within the CMS line, and by ensuring purity of the CMS line, a major source of contamination of the hybrid seeds is removed leading to obvious benefits for the seed industry and farmers.

12 Claims, 16 Drawing Sheets

N: male fertile (N-cytoplasm), S: male sterile (S-cytoplasm)

N: male fertile (N-cytoplasm)
S: male sterile (S-cytoplasm)

SEQUENCE LISTING

<160> NUMBER OF SEQ ID NOS: 20

<210> SEQ ID NO 1
<211> LENGTH: 1590
<212> TYPE: DNA
<213> ORGANISM: Capsicum annuum
<220> FEATURE:
<221> NAME/KEY: gene
<222> LOCATION: (223)...(678)
<223> OTHER INFORMATION: orf456

<400> SEQUENCE: 1

```
agcgcggaag cttaagcgga aatgaaagag gaggttgagg ttatgaagtc acttagccgt      60
atactataca aagggaaagg cgtcggtacg gagtcacgtc agctgtggat atagactagg     120
ctataaggaa cggagtctta aactatggac cgagacagat atatagaaag tgtgcagtga     180
gggtgcttgt aaatcactag gtagcctagc tcgacccaag caatgcccaa aagtcccatg     240
tatttctggt taaacaaacc agcaatttcc gacaagtctt tcttcattgg aagagcaaga     300
agcggaacta caacatttac atgcaatttc accatgaatt ttattgatta tggcacattg     360
tttacttttt cttttatct cggtatttca atcggcattt ttgcgggccg ttttttgag      420
cgaagtgaag ttttacagga attggagaac ttccagctag aaaaaataaa actgaaaacg     480
gaagcagaac tgcaatttct ttgtagagag cacttgagaa tgaatgaaga attacaatta     540
cctgttccag atggaacgag tatgcacatc tccgactttt tagggaaagc cttttttggtc    600
gacgagactg tgagggaacg aatattaggg ctgactcaaa tttatatgga tctaaaaaac     660
aatggagcaa ccgagtaact tttttctttt attttttagac tattatagca atttgtttag    720
cgctttttaa tatattcgtc tgtcgccgtt gcagctaaaa taacggagga tggaggcggg     780
gaggggaggg ggacatcaaa tggattcaag tttgaacaaa acaggaagag gttcgattcc     840
tctttgatgt tgttaagcca agagcgccaa gcgcatgcgc gaaatgagag cgtcaggaat     900
ggaaaggcaa aacctactat gcaccaagtc caggaacccg agtccgagta cagtgaatca     960
aggaagagac tgcagcttca tcagctcaat gcaaggtccg tcgaaatctt ccggagggt     1020
ctagcatccc gtaggtcagt tactccagcg ccacagttcg acagctcggg aaatacctct    1080
cacgcccacg gtcgtctttt gaccacgcaa tgaccttccc agaatgggtt gcagaaagca    1140
gaatctcaaa gggggaaccc catccagggg atatgcagat agagcgccca agacttggca    1200
gggaacggga ccgtgattct gaagaggaac agacaagagg aaagcaaggc caagaagcct    1260
ccgggataga ctcctccctc tatacgtggg agcaacatag acagttcctc ttccctgaag    1320
ccgaggccaa actaacatat cctgtttctc ccgaaacaac ggattcctca ccctcaggag    1380
ccccaagtaa cgaatccgaa tgcctatctc ccgtttaata agacttattg gaatggaaga    1440
aggagagtag tcctctggtc atcagttagt agttcaataa tcccagtagt tgtcctcttg    1500
cctaaaaaaa ggagtcagcc caacatggac aatgataggc agaccaaaga tttacgcagt    1560
ccttgcgtgc ttgctttgcg caccgaattc                                    1590
```

<210> SEQ ID NO 2
<211> LENGTH: 251
<212> TYPE: DNA
<213> ORGANISM: Capsicum annuum

<400> SEQUENCE: 2

```
tgaaaagtgg ttaatagcga gatccattaa ccgtgcttgc tgctctgcgt tgaactcctt      60
```

```
tagtggcttc gctcgctcgc tctaacgctc gtttagtaga cagcgagtgg agtgcataag      120
cccctttaga datagggggtg agtactacac gagctcgtaa gtaaagtacg gaacgagcct      180
tgtctacgaa gcagagcgac ctcatcttgc ttgcttctgg cgaagcttct agctctaaat      240
aataggaatt c                                                           251
```

```
<210> SEQ ID NO 3
<211> LENGTH: 162
<212> TYPE: DNA
<213> ORGANISM: Saccharomyces cerevisiae

<400> SEQUENCE: 3
```

```
atgctttcac tacgtcaatc tataagattt ttcaagccag ccacaagaac tttgtgtagc      60
tctagatatc tgcttcagca aaaacccgtg gtgaaaactg cccaaaactt agcagaagtt      120
aatggtccag aaactttgat tggtcctggt gctaaagagg gt                          162
```

```
<210> SEQ ID NO 4
<211> LENGTH: 720
<212> TYPE: DNA
<213> ORGANISM: Artificial Sequence
<220> FEATURE:
<223> OTHER INFORMATION: green fluorescent protein variant

<400> SEQUENCE: 4
```

```
atgtgagcaa gggcgaggag ctgttcaccg gggtggtgcc catcctggtc gagctggacg      60
gcgacgtaaa cggccacaag ttcagcgtgt ccggcgaggg cgagggcgat gccacctacg      120
gcaagctgac cctgaagttc atctgcacca ccggcaagct gcccgtgccc tggcccaccc      180
tcgtgaccac cctgacctac ggcgtgcagt gcttcagccg ctaccccgac cacatgaagc      240
agcacgactt cttcaagtcc gccatgcccg aaggctacgt ccaggagcgc accatcttct      300
tcaaggacga cggcaactac aagacccgcg ccgaggtgaa gttcgagggc gacaccctg      360 gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720
```

```
<210> SEQ ID NO 5
<211> LENGTH: 25
<212> TYPE: DNA
<213> ORGANISM: Artificial Sequence
<220> FEATURE:
<223> OTHER INFORMATION: forward primer in inverse PCR for 3' flanking
      region of coxII gene

<400> SEQUENCE: 5
```

```
cttggctggt agaaccactc tattg                                            25
```

```
<210> SEQ ID NO 6
<211> LENGTH: 26
<212> TYPE: DNA
<213> ORGANISM: Artificial Sequence
<220> FEATURE:
<223> OTHER INFORMATION: reverse primer in inverse PCR for 3' flanking
      region of coxII gene
```

```
<400> SEQUENCE: 6
gaaggagttt actatggtca gtgcag                                          26

<210> SEQ ID NO 7
<211> LENGTH: 35
<212> TYPE: DNA
<213> ORGANISM: Artificial Sequence
<220> FEATURE:
<223> OTHER INFORMATION: forward primer in inverse PCR for 5' and 3'
      flanking regions of apt6 gene

<400> SEQUENCE: 7
aggattgcca agcatttggt actgagtttc ctcct                                35

<210> SEQ ID NO 8
<211> LENGTH: 35
<212> TYPE: DNA
<213> ORGANISM: Artificial Sequence
<220> FEATURE:
<223> OTHER INFORMATION: reverse primer in inverse PCR for 5' and 3'
      flanking regions of apt6 gene

<400> SEQUENCE: 8
ggtatgatac cttatagctt acacgttaca agtca                                35

<210> SEQ ID NO 9
<211> LENGTH: 21
<212> TYPE: DNA
<213> ORGANISM: Artificial Sequence
<220> FEATURE:
<223> OTHER INFORMATION: coxII RT 5' primer

<400> SEQUENCE: 9
atgcccaaaa gtcccatgta t                                               21

<210> SEQ ID NO 10
<211> LENGTH: 20
<212> TYPE: DNA
<213> ORGANISM: Artificial Sequence
<220> FEATURE:
<223> OTHER INFORMATION: coxII RT 3' primer

<400> SEQUENCE: 10
ttactcggtt gctccattgt                                                 20

<210> SEQ ID NO 11
<211> LENGTH: 23
<212> TYPE: DNA
<213> ORGANISM: Artificial Sequence
<220> FEATURE:
<223> OTHER INFORMATION: primer for sequencing

<400> SEQUENCE: 11
tgcttgtaaa tcactaggta gcc                                             23

<210> SEQ ID NO 12
<211> LENGTH: 22
<212> TYPE: DNA
<213> ORGANISM: Artificial Sequence
<220> FEATURE:
<223> OTHER INFORMATION: primer for sequencing

<400> SEQUENCE: 12
ccagcaattt ccgacaagtc tt                                              22
```

```
<210> SEQ ID NO 13
<211> LENGTH: 24
<212> TYPE: DNA
<213> ORGANISM: Artificial Sequence
<220> FEATURE:
<223> OTHER INFORMATION: primer for sequencing

<400> SEQUENCE: 13
aacgagtatg cacatctccg actt                                            24

<210> SEQ ID NO 14
<211> LENGTH: 23
<212> TYPE: DNA
<213> ORGANISM: Artificial Sequence
<220> FEATURE:
<223> OTHER INFORMATION: primer for sequencing

<400> SEQUENCE: 14
ttaggcaaga ggacaactac tgg                                             23

<210> SEQ ID NO 15
<211> LENGTH: 21
<212> TYPE: DNA
<213> ORGANISM: Artificial Sequence
<220> FEATURE:
<223> OTHER INFORMATION: coxII SCAR PCR primer

<400> SEQUENCE: 15
gtcgggagaa ctacctaact a                                               21

<210> SEQ ID NO 16
<211> LENGTH: 23
<212> TYPE: DNA
<213> ORGANISM: Artificial Sequence
<220> FEATURE:
<223> OTHER INFORMATION: coxII SCAR PCR primer

<400> SEQUENCE: 16
ggctacctag tgatttacaa gca                                             23

<210> SEQ ID NO 17
<211> LENGTH: 27
<212> TYPE: DNA
<213> ORGANISM: Artificial Sequence
<220> FEATURE:
<223> OTHER INFORMATION: apt6I SCAR PCR primer

<400> SEQUENCE: 17
agtccacttg aacaatttga ataatc                                          27

<210> SEQ ID NO 18
<211> LENGTH: 22
<212> TYPE: DNA
<213> ORGANISM: Artificial Sequence
<220> FEATURE:
<223> OTHER INFORMATION: apt6I SCAR PCR primer

<400> SEQUENCE: 18
gttccgtact ttacttacga gc                                              22

<210> SEQ ID NO 19
<211> LENGTH: 25
<212> TYPE: DNA
<213> ORGANISM: Artificial Sequence
<220> FEATURE:
<223> OTHER INFORMATION: primer for coxII positive control
```

```
<400> SEQUENCE: 19
cttggctggt agaaccactc tattg                                        25

<210> SEQ ID NO 20
<211> LENGTH: 26
<212> TYPE: DNA
<213> ORGANISM: Artificial Sequence
<220> FEATURE:
<223> OTHER INFORMATION: primer for coxII positive control

<400> SEQUENCE: 20
gaaggagttt actatggtca gtgcag                                       26
```

DNA FRAGMENT SPECIFIC TO CYTOPLASMIC MALE STERILE PEPPER AND USE THEREOF

CROSS-REFERENCE TO RELATED APPLICATIONS

This is a national stage application of PCT/KR2004/001063, filed May 7, 2004, which is incorporated herein by reference in its entirety, and also claims the benefit of Patent Application No. PCT/KR03/100904 filed May 7, 2003 and Korean Priority Application No. 10-2003-0029269, filed May 9, 2003.

TECHNICAL FIELD

The present invention relates to a DNA fragment specific to cytoplasmic male sterile pepper, a method for distinguishing the cytoplasmic genotype of plant using said DNA based markers, and a method for preparing a transgenic cytoplasmic male sterile plant.

BACKGROUND ART

Hybrid vigor is a phenomenon by which the progeny of a cross between two inbred lines has a higher yield potential than either one of the parents. Hybrids can yield up to 10-30% more than the best non-hybrid varieties, and are a favored option for increasing yield.

The most widely used system for hybrid pepper production is the three line system: (a) a male sterile and female fertile line called the cytoplasmic male sterile (CMS) line because it carries a male sterility-conferring mutation in the cytoplasmic component of the genome; (b) a maintainer line; and (c) a restorer line. The maintainer and restorer lines are male fertile as well as female fertile. The CMS and maintainer lines are practically identical with respect to the nuclear component of the genome (and are often referred to as iso-nuclear lines) but differ from each other with respect to the cytoplasmic component of the genome. The male sterility of the CMS line is maternally inherited and is most likely due to a mutation in the mitochondrial DNA. The CMS line, being female fertile, can be propagated by fertilization with pollen emanating from the maintainer line. Since the cytoplasmic component of the genome is not transferred through pollen, the progeny of such a cross would inherit the cytoplasm only from the CMS line and would therefore be male sterile. The nuclear component of the genome of the progeny would also be identical to that of the CMS line, even though half of it is inherited from the maintainer line, as there is no difference between these two lines with respect to this component of the genome.

The hybrid seeds are produced in a cross of the CMS line with another inbred parental line, called the restorer line, which as indicated above is male fertile and female fertile. In this cross, the CMS line serves as the female parent while the restorer line is the male parent. The restorer line also carries Rf (restorer of fertility) gene/s in its nuclear genome which will restore male fertility to a plant whose cytoplasm has been inherited from the CMS line. The hybrid seeds therefore would be produced. The CMS and restorer lines are appropriately chosen such that the hybrids exhibit sufficient hybrid vigor (or heterosis) to produce substantially higher yields than inbred varieties.

The CMS in pepper (*Capsicum annuum* L.) was first documented by Peterson (Peterson P A (1958) "Cytoplasmically inherited male sterility in *Capsicum*." Amer Nat., 92:111-119) for PI 164835, which was introduced from India. Since then, commercial seed companies have utilized this trait to produce hybrid $F_1$, seeds in the field. Male sterile (S-) cytoplasm of Peterson's lines is the only common source of CMS used to produce hybrid $F_1$ pepper seeds.

One example of a well-characterized CMS system is found in maize. By screening an mtDNA library from cms-T maize with sterile and fertile mtRNA, Dewey et al. (Dewey R E, Levings III C S, Timothy D H (1986) "Novel recombination in the maize mitochondrial genome produces a unique transcriptional unit in the Texas male-sterile cytoplasm." Cell 44: 439-449) identified a region specific to T-cytoplasm. Said region contains an unusual gene, designated as T-urf13, which is predicted to encode a 13-kDa polypeptide (URF13). T-urf13 is positioned upstream of orf25 and is co-transcribed.

Another example is found in the genus *Petunia*. The S-pcf gene has been detected in correlation with CMS in Petunias. This locus consists of the 5' portion of atp9 gene; the exon part of coxII; and an unknown open reading frame, urf-s (Young E G, Hanson M R (1987) "A fused mitochondrial gene associated with cytoplasmic male sterility is developmentally regulated." Cell 50: 4149).

The specific genes correlated with CMS have also been reported in beans (Johns C, Lu M, Lyznik A, Mackenzie S (1992) "A mitochondrial DNA sequence is associated with abnormal pollen development in cytoplasmic male sterile bean plants." The Plant Cell 4: 435-449), *Brassica* (Grelon M, Budar F, Bonhomme S, Pelletier G (1994) "Ogura cytoplasmic male-sterility (CMS)-associated orf138 is translated into a mitochondrial membrane polypeptide in male-sterile *Brassica* cybrids." Mol Gen Genet 243: 540-547), radishes (Makaroff C A, Apel I J, Palmer J D (1990) "Characterization of radish mitochondrial atpA-associated sequences and relationship with male sterility." Plant Mol Biol 15: 735-746), sunflowers (Moneger R, Smart C J, Leaver C J (1994) "Nuclear restoration of cytoplasmic male sterility in sunflower is associated with the tissue-specific regulation of a novel mitochondrial gene." The EMBO J. 13(1): 8-17), rice (Akagi H (1995) "Genetic diagnosis of cytoplasmic male sterile cybrid plants of rice." Theor. Appl. Genet. 90:948-951), carrots (Kanzaki H, Takeda M, Kameya T (1991) "Sequence analysis of a mitochondrial DNA fragment isolated from cultured cells of carrot cytoplasmic male-sterile strain." Japanese J Genet 66: 719-724), and *sorghum* (Tang H V (1996) "Transcript processing internal to a mitochondrial open reading frame is correlated with fertility restoration in male-sterile *Sorghum*." Plant J. 10:123-133).

Although these CMS-associated genes are commonly generated by intra-rearrangement of mtDNA (Hanson M R (1991) "Plant mitochondrial mutations and male sterility." Annu Rev Genet 25:461-486), the open reading frames share no significant sequence homology. How these genes may act in CMS plants and result in mitochondrial dysfunction and non-functional pollens has not been known until now.

CMS traits are commercially very useful and important in hybrid $F_1$, seed production. This is why transgenic male sterile plants have been attempted and developed by several research groups. For example, Mariani et al. (Mariani C, Beuckeleer J, Trueftner J, Leemans J, Goldberg R B (1990) "Induction of male sterility in plants by a chimeric ribonuclease gene." Nature 347:737-741) have developed male sterile tobacco by using a tapetum-specific promoter and barnase gene, which functions as a ribonuclease gene in plants. Several experiments have been also attempted to transform these CMS-associated genes into fertile plants. The orf239, CMS-associated mitochondrial DNA sequence in the common bean (Abad A R, Mehrtens B J, Mackenzie S A (1995) "Specific expression in reproductive tissues and fate of a mitochondrial sterility-associated protein in cytoplasmic male sterile beans." Plant Cell 7:271-285) was used to transform tobacco with or without a mitochondrial targeting sequence. Transformed tobacco exhibited a semi-sterile or male-sterile phenotype even though targeting of the protein to mitochondria has not been made (He S, Abad A R, Gelvin S B, Mackenzie S A (1996) "A cytoplasmic male sterility-associated mitochondrial protein causes pollen disruption in transgenic tobacco." Proc. Natl. Acad. Sci. USA 93:11763-11768). Another CMS-associated gene, urf-s sequence of the pcf gene which encodes the 25 kDa protein in the genus *Petunia*, had been transformed to petunia and tobacco plants with constructs of mitochondrial targeting sequences. Even though expression of PCF protein was detected in mitochondria of transgenic petunia and tobacco plants, the fertility of the plants was not affected (Wintz H, Chen H C, Sutton C A, Conley C A, Cobb A, Ruth D, Hanson M R (1995) "Expression of the CMS-associated urf-s sequence in transgenic petunia and tobacco." Plant Mol Biol 28:83-92).

In addition, correct identification of male fertile (N-) cytoplasm and male sterile (S-) cytoplasm in plants including food crops is very important in breeding systems. The estimation of hybrid seed purity and cytoplasmic genotype is conventionally done by the grow-out test (GOT), which is based on the assessment of morphological and floral characteristics (that distinguish the hybrid) in a representative sample of plants that are grown to maturity. For example, pepper plants take several months to reach maturity, and the seeds have to be stored under appropriate conditions as they cannot be marketed until these results become available. In addition, substantial delays can result in the first growing season after hybrid seed production which is taken up by the GOT, which is also the preferred season for hybrid cultivation. In such cases, the seeds have to be stored for up to a year, i.e., until the subsequent growing season, before they can be marketed. For seed companies, large amounts of capital are therefore locked in the form of hybrid seed stocks for prolonged periods while awaiting the results of the GOT. Another disadvantage of the GOT is that it can be subjective due to environmental influences on the expression of morphological characteristics. Further, there is also the possibility that adverse climatic conditions (such as heavy wind or rain, high temperatures, drought) can damage or destroy the crop and make it difficult to collect the data. In order to solve the above problems, a technique using the CMS-associated sequence as a DNA marker has been developed to easily detect a male sterile cytoplasmic type. This technique uses a DNA marker that is detected by Polymerase Chain Reaction (PCR), and it is ideally suited for this purpose as it is much more efficient for handling large numbers of samples than hybridization-based methods like Restriction Fragment Length Polymorphisms (RFLPs).

DISCLOSURE

Technical Problem

To solve the problems of the prior art, it is an aspect of the present invention to provide a DNA fragment associated with cytoplasmic male sterility in pepper.

It is another object of the present invention is to provide a construct for use in obtaining a transgenic male-sterile plant using a polynucleotide consisting of the $223^{rd}$ to $678^{th}$ nucleic acid of SEQ ID NO: 1, and a DNA sequence capable of targeting the protein expressed by said coding region into the mitochondrion.

It is another object of the present invention is to provide a method for producing a transgenic male sterile plant.

It is another object of the present invention is to provide a method for inhibiting the production of pollen in a transgenic plant.

It is another object of the present invention is to provide nucleotide sequences specific to CMS pepper.

It is another object of the present invention is to provide a method for identifying male sterility in pepper by the PCR method.

It is another object of the present invention is to provide a PCR primer set for identifying male sterility in pepper.

Technical Solution

In order to accomplish the aspects of the present invention, the present invention provides a DNA fragment specific to cytoplasmic male sterile pepper comprising a polynucleotide of SEQ ID NO: 1 or a polynucleotide consisting of the $223^{rd}$ to $678^{th}$ nucleic acid of SEQ ID NO:1.

Further, the present invention provides a transgenic male sterile plant comprising a polynucleotide sequence consisting of the $223^{rd}$ to $678^{th}$ nucleic acid of SEQ ID NO:1.

Further, the present invention provides a construct for use in obtaining a transgenic male sterile plant, comprising:

a) a polynucleotide sequence (named orf456) consisting of the $223^{rd}$ to $678^{th}$ nucleic acid of SEQ ID NO:1.

b) a promoter that is active in the plant, and is operably linked to the polynucleotide to achieve expression thereof; and c) a DNA sequence capable of transferring the protein expressed by the polynucleotide of a) to the mitochondrion.

Further, the present invention provides a method for producing transgenic male sterile plants comprising:

a) preparing a construct comprising i) a polynucleotide sequence (named orf456) consisting of the $223^{rd}$ to $678^{th}$ nucleic acid of SEQ ID NO:1, ii) a promoter that is active in the plant, and that is operably linked to the polynucleotide so as to achieve expression thereof, and iii) a DNA sequence capable of transferring the protein expressed by the polynucleotide of a) to the mitochondrion; and b) transforming the construct into a plant or plant cell.

Further, the present invention provides a method for inhibiting the production of pollen in a plant, comprising:

a) preparing a construct comprising i) a polynucleotide sequence (named orf456) consisting of the $223^{rd}$ to $678^{th}$ nucleic acid of SEQ ID NO:1, ii) a promoter that is active in the plant, and that is operably linked to the polynucleotide so as to achieve expression thereof, and iii) a DNA sequence capable of transferring the protein expressed by the polynucleotide of a) to the mitochondrion; and b) transforming the construct into a plant or plant cell.

Further, the present invention provides a CMS specific DNA fragment (SEQ ID NO:1, 1596 bp) at the 3' flanking region of coxII in pepper for identifying a male sterile pepper by PCR, comprising:

a) conducting a Polymerase Chain Reaction (PCR) with a forward primer capable of annealing a part of a coxII genome gene or a part of a nucleotide sequence of SEQ ID NO:1, and a reverse primer capable of annealing a part of a nucleotide sequence of SEQ ID NO:1 on plant DNA or plant mitochondrial DNA; and b) observing whether DNA fragment is amplified or not, and wherein the presence of amplified fragments indicates that the plant is a male sterile line, and the absence of the same indicates that the plant is a male fertile line.

Further, the present invention provides a method for identifying male sterility in a plant comprising:

a) conducting a Polymerase Chain Reaction (PCR) with a forward primer capable of annealing a part of the atp6 genome gene or a part of a nucleotide sequence of SEQ ID NO:2, and reverse primer capable of annealing a part of a nucleotide sequence of SEQ ID NO:2 on plant DNA or plant mitochondrial DNA; and b) observing whether a DNA fragment is amplified or not, and wherein the presence of the amplified fragments indicates that the plant is a male sterile line, and the absence of the same indicates that the plant is a male fertile line.

Further, the present invention provides a PCR primer set for identifying male sterility in a plant comprising:

a) a forward primer capable of annealing a part of a coxII genome gene or a part of a nucleotide sequence of SEQ ID NO:1; and b) a reverse primer capable annealing of a part of a nucleotide sequence of SEQ ID NO:1 on plant DNA or plant mitochondrial DNA, and wherein the size of the amplified DNA fragment is from 50 bp to over 2 kbp.

Further, the present invention provides a CMS specific DNA fragment (SEQ ID NO:2, 251 bp) at the 3' flanking region of atp6 in pepper for identifying a male sterile pepper by PCR, comprising:

a) a forward primer capable of annealing a part of an apt6 genome gene or a part of a nucleotide sequence of SEQ ID NO:2; and b) a reverse primer capable of annealing a part of a nucleotide sequence of SEQ ID NO:2 on plant DNA or plant mitochondrial DNA, and wherein the size of the amplified DNA fragment is from 50 bp to over 1 kb kbp.

MODE FOR INVENTION

Figure 1:
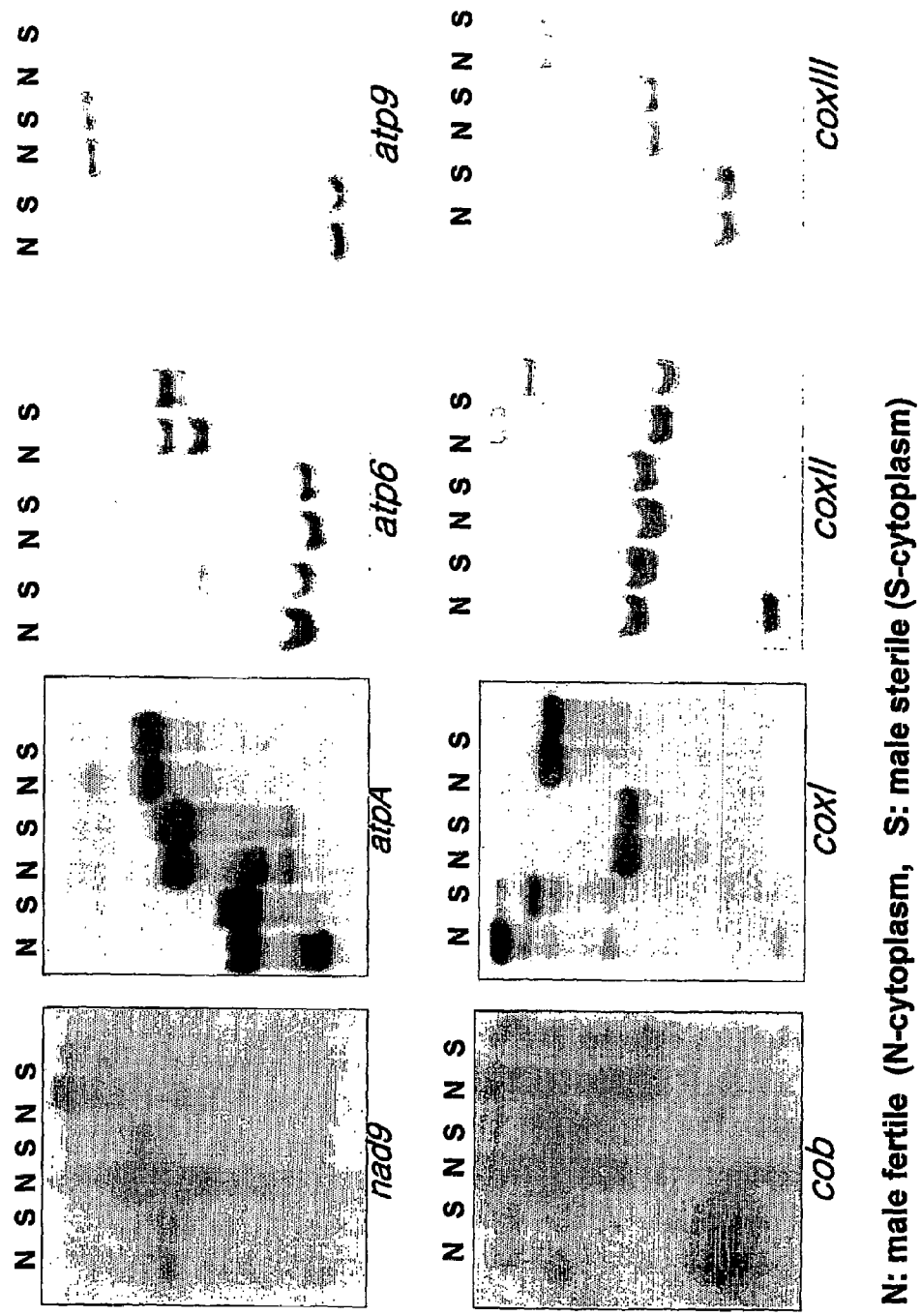
FIG. 1 shows a Southern-blot analysis of mtDNAs digested with EcoRI, HindIII, and BamHI hybridized with eight mitochondrial probes (coxI, coxII, coxIII, atpA, atp6, atp9, cob, nad9 genes) to compare male fertile (F) and male sterile (S) lines in *C. annuum* L.

In the following detailed description, only selected embodiments of the invention have been shown and described, simply by way of illustration of the best mode contemplated by the inventors of carrying out the invention. As will be realized, the invention may be modified in various respects, all without departing from the invention. Accordingly, the drawings and description are to be regarded as illustrative in nature, and not restrictive.

A DNA fragment specific to cytoplasmic male sterile pepper of the present invention includes a polynucleotide of SEQ ID NO: 1, a polynucleotide consisting of the $223^{rd}$ to $678^{th}$ nucleic acid of SEQ ID NO:1, or a polynucleotide of SEQ ID NO: 2. The polynucleotide of SEQ ID NO: 1 (1596 bp) is located at the 3'-terminal of coxII gene and contains the orf456 region at positions 223 to 678 of the nucleic acids as an open reading Frame. The polynucleotide of SEQ ID NO: 2 (251 bp) is located at the 3'-terminal of the 3'-truncated apt6 gene.

The DNA fragment specific to cytoplasmic male sterile pepper can be used for preparing a male sterile plant or/and distinguishing a male sterile line from a maintainer pepper line.

The present invention could be applied to all kinds of plants, and it preferably includes solanaceae like pepper, eggplant, tobacco, tomato, and petunia; Brassicaceae like turnip, cauliflower, and broccoli; floral plant species like lily and chrysanthemum; and woody plants.

For preparing the transgenic male sterile plant, an expression construct with the DNA fragment (orf456) associated with cytoplasmic male sterility in pepper, wherein the DNA fragment is operably linked to and under the regulatory control of a transcriptional and translational regulatory sequence can be prepared. The transcriptional and translational regulatory sequences are those which can function in specific organisms (i.e., bacteria, yeast, fungi, plant, insects, animals, and humans), cells or tissues that effect the transcriptional and translational expression of the foreign gene with which they are associated, and that can be employed according to the host cell. Examples of transcriptional and translational regulatory sequences include a promoter, an enhancer, a targeting presequence, and a terminator, but they are not limited thereto.

The promoter can be derived from a highly-expressed gene to direct transcription of a downstream structural sequence. Such promoters can be derived from a public plasmid or vector, and examples include a RA8 promoter, a TA29 promoter, and so on. Selection of the appropriate promoter is well within the level of ordinary skill in the art.

The expression construct can further include a multi-cloning site, a selectable marker, origins of replication, and a DNA sequences capable of transferring the protein expressed by the foreign gene to the mitochondrion, for example, a presequence of subunit IV of the yeast cytochrome c oxidase (coxIV) of SEQ ID NO: 3. The expression construct may be a common vector, and examples are a plasmid or viral vector including the pCAMBIA2300 vector which consists of the CaMV 35S promoter and the terminator of the nopaline synthase (nos) gene. However, any other plasmid or vector may be used as long as it is replicable and viable in the host.

Transformation methods for generating transformants according to the host cell type are well known, e.g. calcium phosphate transfection, DEAE-Dextran mediated transfection, electrophoration (Davis, L., Dibner, M., Battey, I., *Basic Methods in Molecular Biology,* 1986), heat-shock, *Agrobacterium tumefaciens*-mediated DNA transfer, protoplast transformation, microinjection, and biolistic transfection.

In one embodiment of the present invention, recombinant pCAMBIA2300 vectors harboring orf456 fragments were introduced into onions, and into *Arabidopsis* by *Agrobacterium tumefaciens*-mediated DNA transfer. Onion transient expression tests showed that the presequence of subunit IV of the yeast cytochrome c oxidase (coxIV) of SEQ ID NO: 3 is capable of transferring the protein expressed by the foreign gene to the mitochondrion. Transformation to *Arabidopsis thaliana* with recombinant pCAMBIA2300 vector harboring an orf456 fragment showed a male sterile phenotype without pollen.

The subject of the present invention is also a process for restoring male-fertile plants from transgenic male-sterile plants, and in accordance with the invention, is characterized in that it comprises the following steps:

(a) transforming the selected higher plant by introducing at least one copy of the hybrid DNA construct as defined above into a recipient plant by means of a vector plasmid containing said sequence, in order to obtain transgenic male-sterile plants (TMSP); (b) transforming the same higher plant as in (a) by introducing at least one copy of an antisense hybrid DNA construct, including the antisense coding region of the orf456 gene by means of a plasmid containing the reverse orf456 sequence, in order to obtain transgenic male-fertile plants (TMFP); and crossing the transgenic male-sterile plants obtained in (1) and the male-fertile plants obtained in (2), in order to obtain vigorous hybrids whose male fertility has been restored and which have pre-selected characteristics. The subject of the present invention also concerns plasmids including an antisense hybrid sequence, as defined above, associated with a promoter chosen from among the constitutive promoters and the promoters specific for the anthers and also associated with a suitable terminator.

In addition, a DNA fragment specific to cytoplasmic male sterile pepper of the present invention can be used for identifying a male sterile pepper from a maintainer pepper. The method for identifying a male sterile pepper comprises a) conducting polymerase chain reaction (PCR) with a forward primer capable of annealing a part of the coxII genome gene, or the apt6 genome gene, or a part of a nucleotide sequence of SEQ ID NOs:1 or 2 and a reverse primer capable of annealing a part of a nucleotide sequence of SEQ ID NOs:1 or 2 for plant DNA or plant mitochondrial DNA as a template, and b) observing whether the DNA fragment is amplified or not, The presence of the amplified fragments indicates that the plant is a male sterile line, and the absence of the same indicates that the plant is a male fertile line. The size of the amplified DNA fragment may be from 50 bp to over 2 kbp, and the length of the forward primer and the reverse primer may be from 50 bp to over 1 kbp.

In the observing step, whether the DNA fragment is amplified or not can be detected by electrophoresis on agarose gel or polyacrylamide gel followed by ethidium bromide staining. Also, a method employing radio-labeling, colorimetry, chemiluminescence, or fluorescence can be applied to detect PCR products.

In an embodiment of the present invention, a primer comprising a nucleotide sequence of SEQ ID NOs:15 or 17 as a forward primer and a primer comprising a nucleotide sequence of SEQ ID NOs: 16 or 18 as a reverse primer are designed.

The following examples are provided to further illustrate the present invention, and are not intended to limit the invention beyond the limitations set in the appended claims

EXAMPLES

Example 1

RFLP and Northern-blot Analysis Between Male Sterile and Fertile Pepper

The near isogenic male fertile (N/rf/rf genotype), male sterile (S/rf/rf), and restorer (S/Rf/Rf) lines of *Capsicum annuum* cv. Milyang were used in this study. These were provided by Hungnong Seed Company.

1-1. RELP Analysis

To isolate the mtDNA from a maintainer and a CMS plant, young leaves of *C. annuum* were harvested after etiolation and homogenized in 70 ml of homogenizing buffer (0.1 M Tris-HCl pH7.2, 0.5 M mannitol, 0.001 M ethylene glycerolbis (β-aminoethyl ether), N,N,N',N'-tetraacetic acid (EGTA), 0.2% bovine serum albumin (BSA), 0.05% cysteine) per 10 g of samples. Mitochondria were purified by sucrose gradient centrifugation, and then mtDNA was isolated by the DNase I procedure (Sparks R B, Dale R M K (1980) "Characterization of $^3$H-labelled supercoiled mitochondrial DNA from tobacco suspension culture cells." *Mol Gen Genet* 180:351-355).

MtDNA (10 µg) of male fertile and CMS lines were separated on 0.8% agarose gels after digestion with EcoRI (Boehringer Mannheim, Germany) and were transferred to Hybond N+ nylon membranes (Amersham Pharmacia Biotech, NJ, USA). Eight mitochondrial probes (coxI, coxII, coxIII, atpA, atp6, atp9, cob, nad9) were selected for RFLP analysis. Mitochondrial DNA probes were radioactively labeled by random priming with [α-32P] dCTP (Amersham Pharmacia Biotech, NJ, USA). Southern-blot analysis was performed in hybridization buffer (0.75 M NaCl, 0.125 M citric acid, 0.05 M sodium phosphate, 5×Denhardt's solution, 3% dextran sulfate, 2.5 mM EDTA, 0.6% SDS, pH 7.2, 50% formamide) at 42° C. for 24 h. The blots were washed in 2×SSC, 0.1% SDS at 65° C. for 10 min; 1×SSC, 0.05% SDS at 65° C. for 20 min. The blots were exposed to X-ray films (Kodak, USA).

FIG. 1 shows Southern-blot analysis of mtDNAs digested with EcoRI, HindIII, and BamHI hybridized with eight mitochondrial probes (coxI, coxII, coxIII, atpA, atp6, atp9, cob, nad9 genes) to compare male fertile (N) and male sterile (S) lines in *C. annuum* L. Three genes (atpA, atp6, coxII) showed polymorphism between fertile and sterile mtDNAs.

1-2: Northern-Blot Analysis

For Northern-blot analysis, total RNA (20 µg) from sterile, fertile, and restored anther was fractionated on a standard formaldehyde gel (1.2% agarose) and transferred to a Hybond N+ nylon membrane (Amersham Pharmacia Biotech., USA) by capillary blotting (Sambrook et al., 1989). Northern-blot analysis was conducted on these three genes (atpA, atp6, coxII). The blots were hybridized at 60° C. for 16 hrs and the final wash was in 0.5×SSC, 0.1% SDS.

Figure 2:
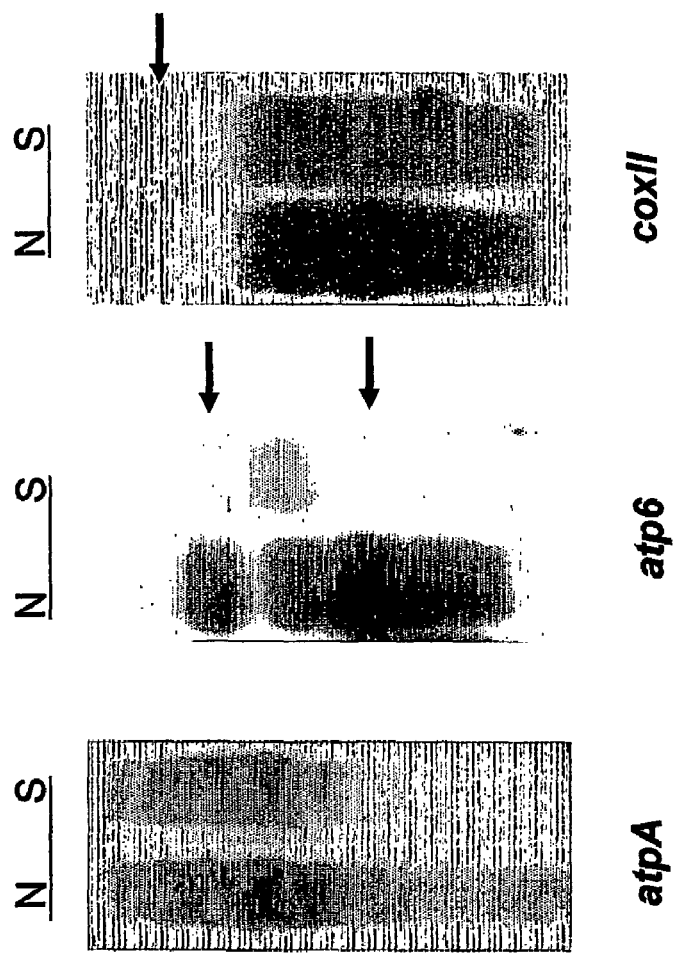
FIG. 2 shows Northern-blot analysis of mtRNAs with three mitochondrial probes (atpA, atp6, coxII). The atp6 and coxII genes show polymorphic band patterns of RNA transcripts (indicated by the arrow).

FIG. 2 shows the result of Northern-blot analysis of mtRNAs with three mitochondrial probes (atpA, atp6, coxII) which show polymorphic bands in Southern-blot analysis. The atp6 and coxII gene show polymorphic band patterns of RNA transcripts (indicated by the arrow).

Example 2

Inverse PCR and Sequencing of Flanking Region of coxII and atp6

2-1. Inverse PCR for 3' Flanking Region of coxII Gene

Inverse PCR was conducted for cloning the 3' region of coxII gene in maintainer and CMS pepper. For inverse PCR, mtDNA (5 µg) was digested overnight at 37° C. in a 100 µl reaction mixture containing 10 units of EcoRI (Boehringer Mannheim, Germany). The digestion mixtures were extracted by phenol/chloroform and the DNA was ethanol-precipitated. Religation of the mtDNA took place for 30 min at 37° C. in 200 µl using 3 units of T4 DNA ligase (BRL, USA). Subsequently, the ligation mixtures were inactivated for 20 min at 65° C. After phenol/chloroform extraction, The DNA was ethanol-precipitated and dissolved in 50 µl TE (10 mM Tris-HCl, 1 mM EDTA, pH 7.4).

PCR was performed on about 500 ng of DNA in a thermocycler (Perkin Elmer 9600) PCR reaction mixture consisted of 25 pmol of each primer (primer set of SEQ ID NOs:5 and 6), 200 µM of each dNTP, 2.5 units of $_{Ex}$Taq DNA polymerase (TakaRa, Japan), and 5 µl of 10×$_{Ex}$Taq DNA polymerase buffer in a total volume of 50 µl. The PCR amplification was at 94° C. (1 min), 60° C. (1 min), and 72° C. (2 min) for 35 cycles. The PCR products were separated on a 1% agarose gel, stained with ethidium bromide, and visualized under ultraviolet light.

2-2. Inverse PCR for 5' and 3' Flanking Region of atp6 Gene

PCR was performed on about 500 ng of DNA in a thermocycler (Perkin Elmer 9600). The PCR reaction mixture consisted of 25 pmol of each primer (primer set of SEQ ID NOs:7 and 8), 200 µM of each dNTP, 2.5 units of $_{Ex}$Taq DNA polymerase (TakaRa, Japan), and 5 µl of 10×$_{Ex}$Taq DNA polymerase buffer in a total volume of 50 µl. The PCR amplification was at 94° C. (1 min), 60° C. (1 min), and 72° C. (2 min) for 35 cycles. The PCR products were separated on a 1% agarose gel, stained with ethidium bromide, and visualized under ultraviolet light.

Figure 3:
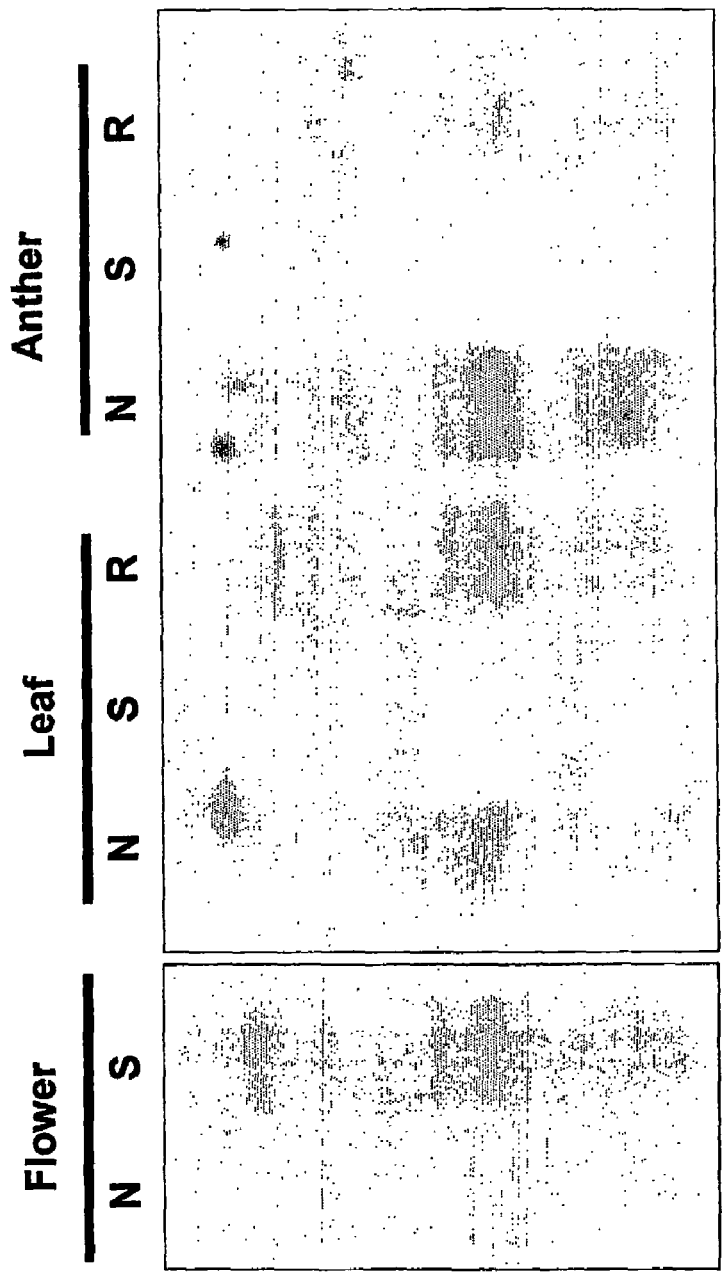
FIG. 3 shows results of RFLP and inverse PCR of atp6 and coxII genes in pepper (*Capsicum annuum* L.). (A): Results of Southern-blot analysis between N-cytoplasm and S-cytoplasm with atp6 (left) and coxII (right) probe. (B): Inverse PCR amplification for cloning of a DNA sequence that is specific to CMS lines of pepper. Predicted PCR fragments are marked with an asterisk (*).

FIG. 3 shows results of RFLP and inverse PCR of atp6 and coxII genes in chili pepper (*Capsicum annuum* L.). "A" is results of Southern-blot analysis between N-cytoplasm and S-cytoplasm with atp6 (left) and coxII (right) probes. MtDNA (10 µg) of maintainer (N-cytoplasm) and CMS (S-cytoplasm) lines were separated on 0.8% agarose gels after digestion with an EcoRI enzyme. "B" is results of inverse PCR amplification for cloning of a DNA sequence that is specific to CMS lines of pepper, and "M1" and "M2" indicates the size markers λ/HindIII and 1 kb DNA puls ladder, respectively (Promega Co. USA). Predicted PCR fragments were marked with an asterisk (*).

2-3. Determination of a Nucleotide that is Specific to CMS Lines of Chili Pepper The amplified products of the 2-1 and 2-2 experiments were separated on 0.8% agarose gel and purified using Gel extraction kits (Qiagen, Germany), cloned to pGEM-T easy vectors (Promega, USA), and sequenced with a Perkin Elmer 9600 PCR machine and an ABI377 automatic sequencer (Applied Biosystems, USA).

Figure 4:
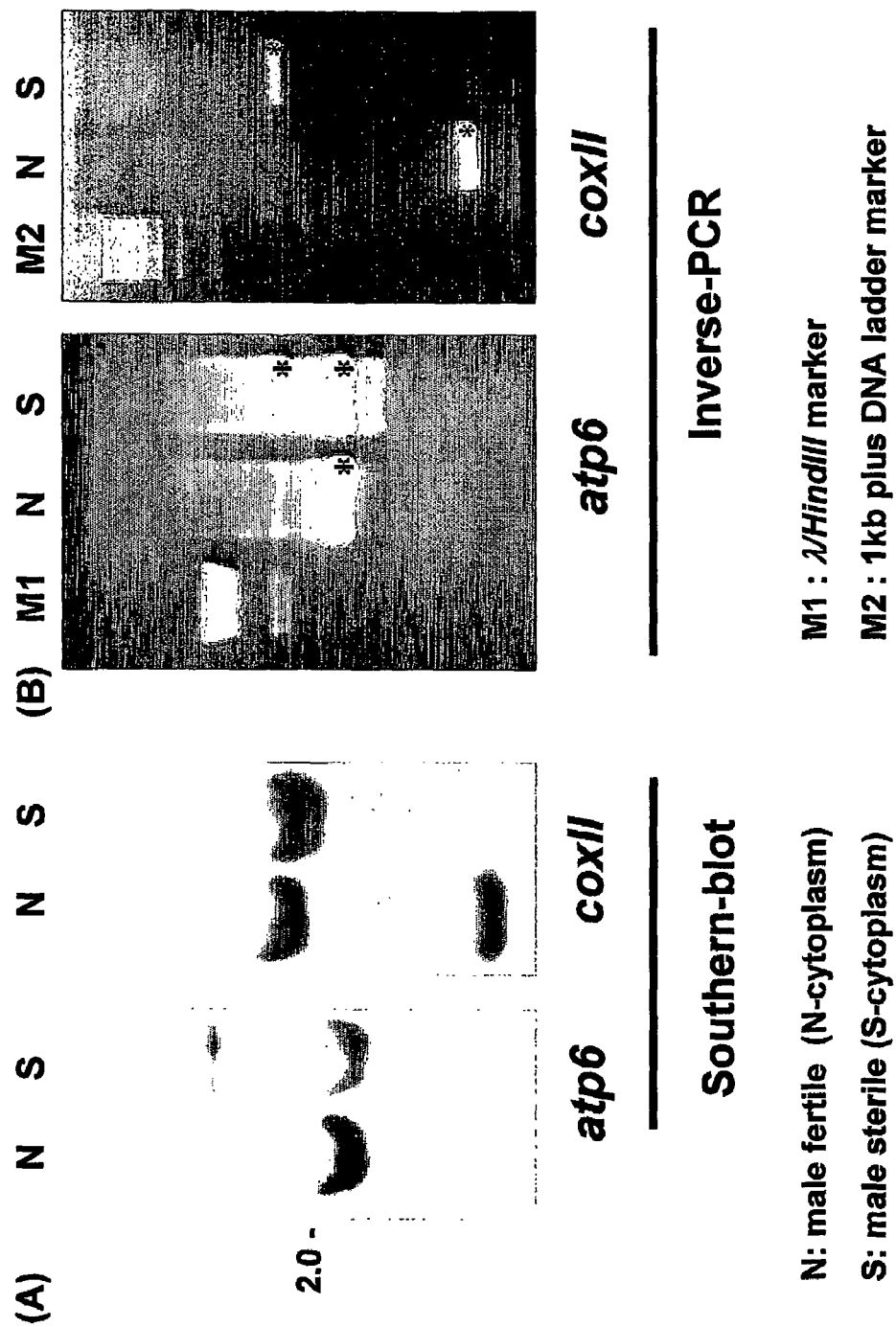
FIG. 4 shows a schematic diagram of coxII coding and a flanking region between a maintainer line (N-cytoplasm) and CMS line (S-cytoplasm) of pepper.

FIG. 4 shows a schematic comparison of coxII coding and flanking region between a maintainer line (N-cytoplasm) and a CMS line (S-cytoplasm) of pepper. The arrow indicates the primer pairs for inverse PCR of the coxII 3' region. EcoRI-EcoRI fragment size of each coxII is indicated on the right side. The CMS specific sequence of the 3' flanking region of coxII is revealed as 1596 bases (SEQ ID No. 1).

Figure 5:
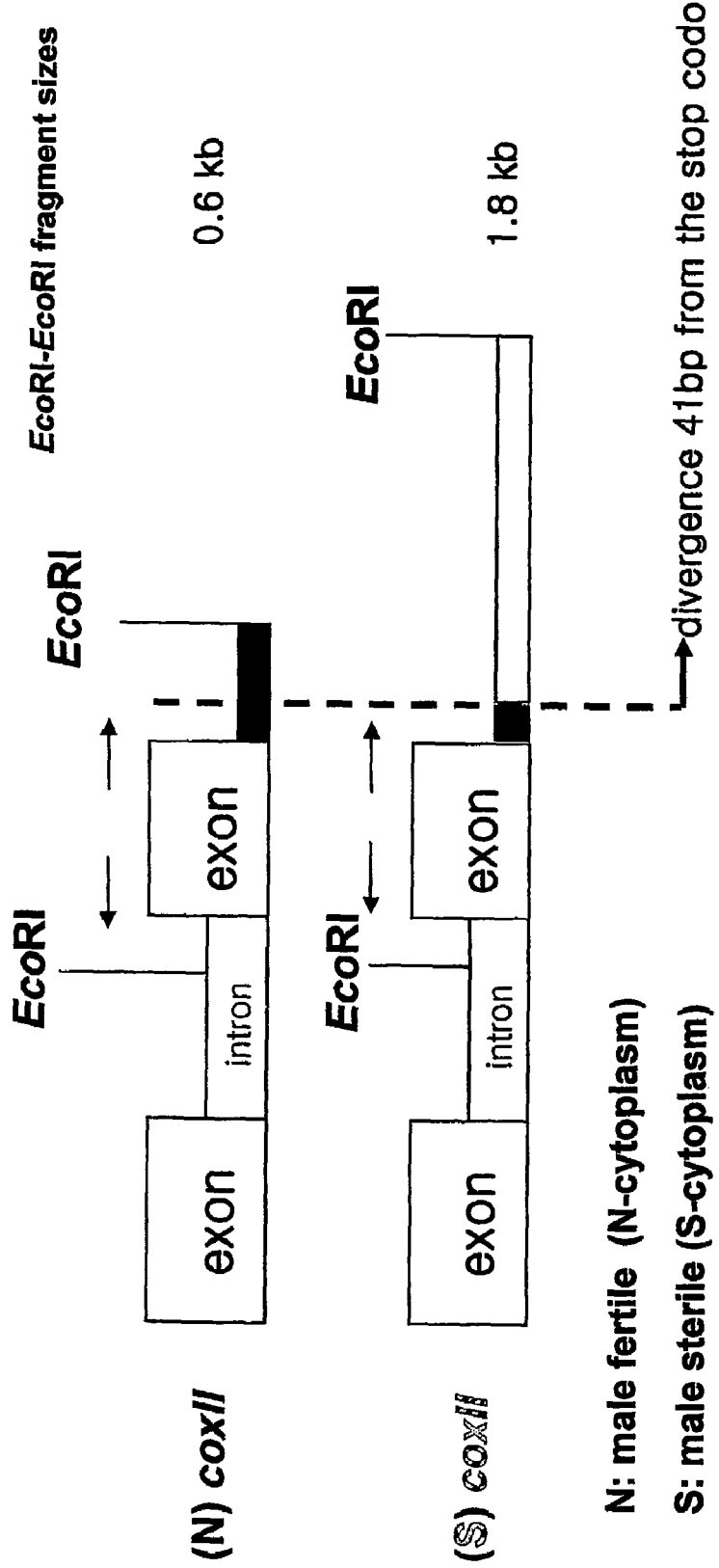
FIG. 5 shows a schematic diagram comparison of atp6 coding and a flanking region between a maintainer line (N-cytoplasm) and a CMS line (S-cytoplasm) of pepper. (A): Schematic representation of the nucleotide sequence comparison of (N) atp6-1 and (S) atp6-1 genes of *C. annuum*. (B): Schematic representation of the nucleotide sequence comparison of the (N) atp6-2 and (S) ψ atp6-2. The highly conserved region is indicated by the green box. The red box shows the truncated region without nucleotide sequence homology with the 3' region of (N) atp6-2. The arrow indicates the primer pairs for inverse PCR of the atp6 3' region. EcoRI-EcoRI fragment sizes of each atp6 copies are indicated at the right side.

FIG. 5 shows a schematic comparison of atp6 coding and flanking region between a maintainer line (N-cytoplasm) and a CMS line (S-cytoplasm) of pepper. "A" is a schematic structural comparison of (N) atp6-1 and (S) atp6-1 genes of *C. annuum*, and "B" is a schematic structural comparison of the (N) atp6-2 and (S) ψ atp6-2. The highly conserved regions are indicated by the green box. The red box shows the truncated region which has no nucleotide sequences homology with the 3' region of (N) atp6-2. The arrow indicates the primer pairs for the inverse PCR of the atp6 3' region. EcoRI-EcoRI fragment sizes of each of the atp6 copies are indicated on the right side. The CMS specific sequence of the 3' flanking region of atp6 gene is revealed as 251 bases (SEQ ID No. 2).

4-4. Identification of Candidate Open Reading Frame Associated to CMS in Pepper

Figure 6:
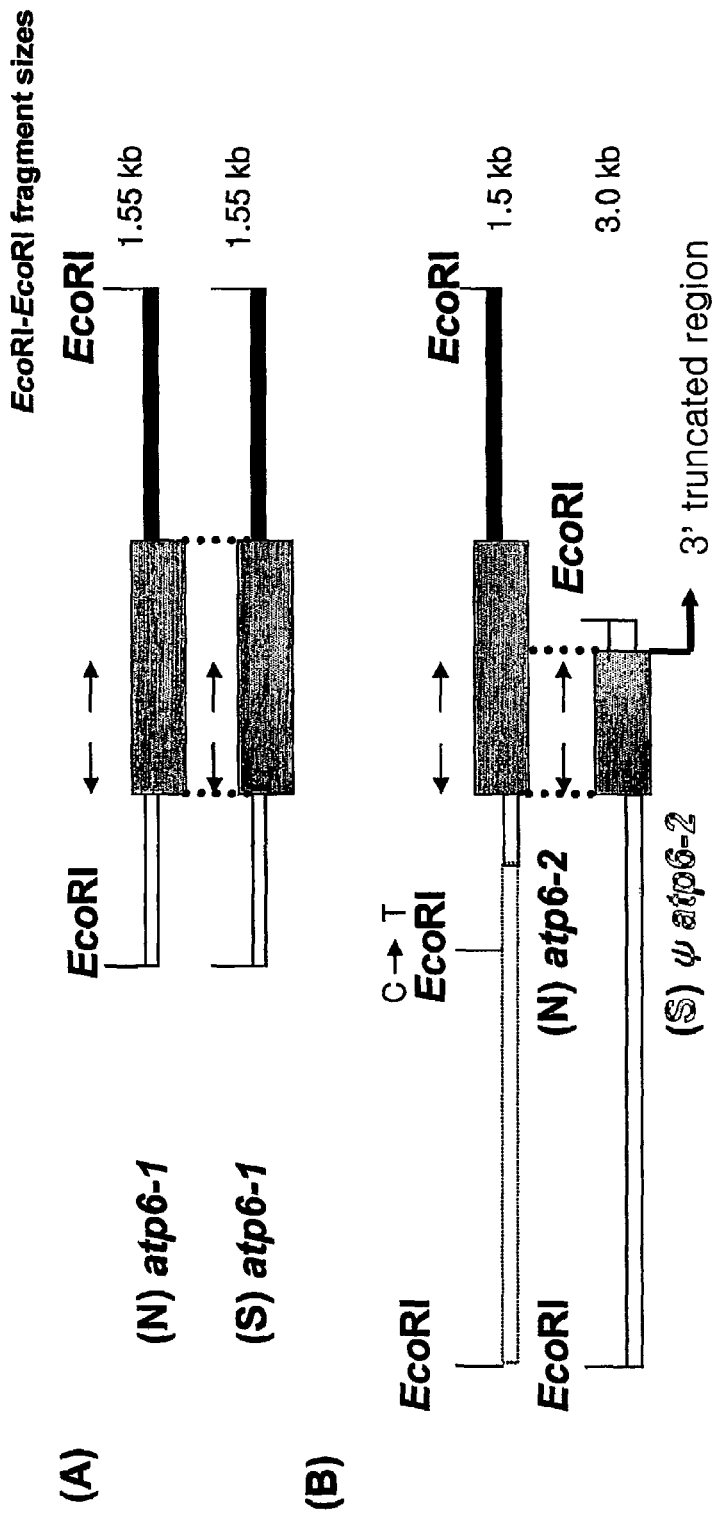
FIG. 6 shows a schematic representation of the nucleotide sequence comparison of the coxII gene between a fertile line and a sterile line. The arrow indicates the primer pairs for inverse PCR, sequencing, and RT-PCR experiments on the coxII 3' region.

A new open reading frame was found by the program ORF Finder in the NCBI homepage. By inverse PCR and sequencing results, the difference in the structure of coxII gene between fertile and sterile pepper was drawn and the presence of a new open reading frame, named orf456, was detected at the 3' region of the coxII gene in the sterile line (FIG. 6). In the case of the atp6 gene, no new open reading frame or chimeric gene were detected in atp6 coding and flanking regions.

Example 3

Cloning for 3' Region of coxII Gene 3-1. Reverse-transcriptase PCR Experiments

To investigate whether the open reading frame presumed by the ORF Finder program was really transcribed in a CMS plant, RT-PCR with specific primer pairs (SEQ ID NOs: 6, 9 and 10) was performed. Three micrograms of total anther RNA was used in a 10 μl reaction of first strand cDNA synthesis driven by M-MLV reverse transcriptase (Gibco BRL, USA), according to the protocols given by the manufacturer. PCR was performed on 1 μl cDNA in a thermocycler (PerkinElmer 9600) using 10 pmol of each primer, 100 μM of each dNTP, 1.5 units of $_{Ex}$Taq DNA polymerase (TaKaRa, Japan), and 2.5 μl of 10×$_{Ex}$Taq DNA polymerase buffer in a 25 μl. The PCR amplification was at 94° C. (1 min), 50° C. (1 min), and 72° C. (2 min) for 30 cycles. RT-PCR products were cloned to pGEM-T easy vectors (Promega, USA), and sequenced with T7 and SP6 primers (SEQ ID NOs:11-14).

Figure 7:
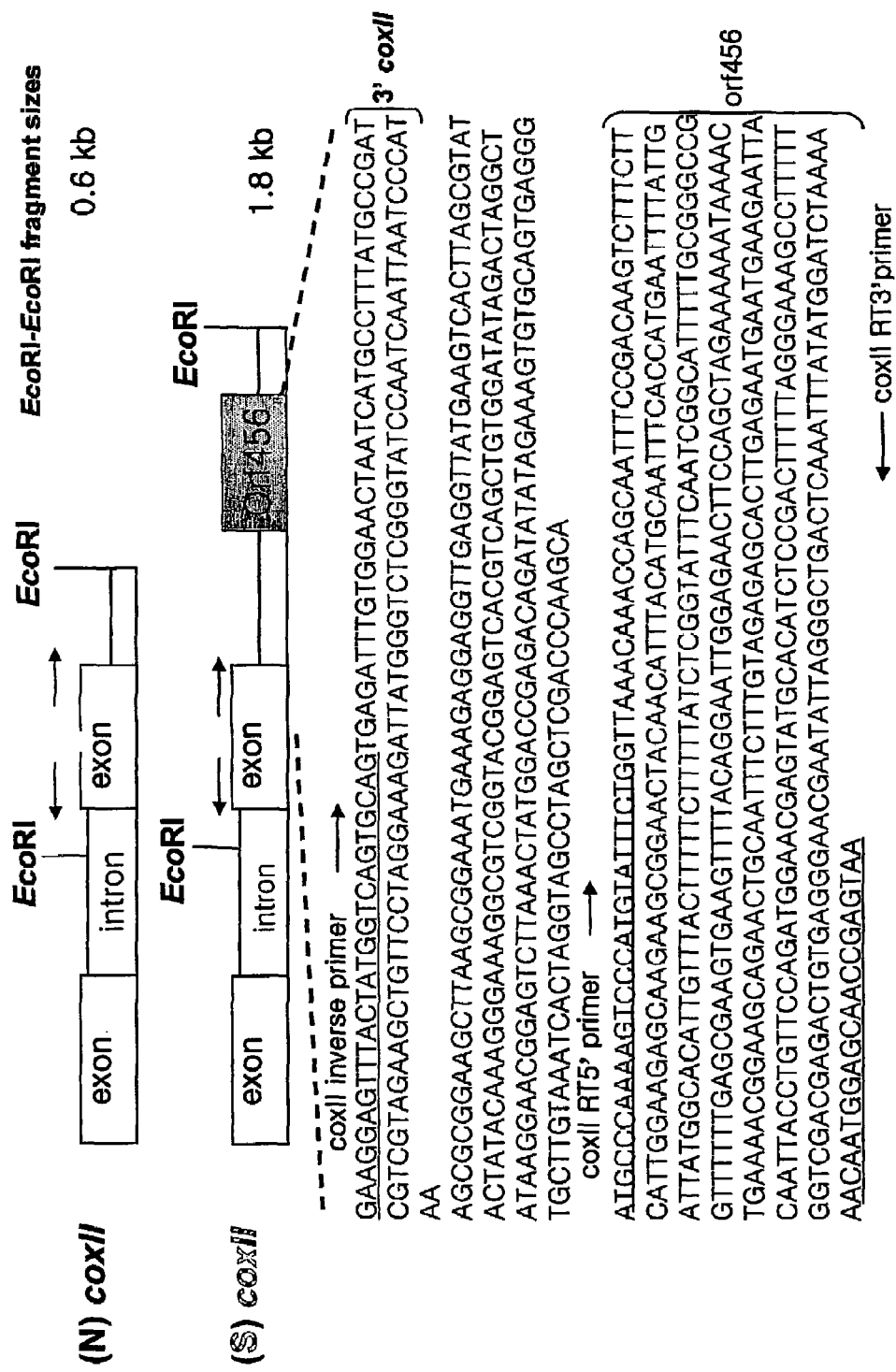
FIG. 7 shows the results of RT-PCR experiments on the orf456 gene which is located on the 3' region of the coxII gene in a sterile line.
Figure 8:
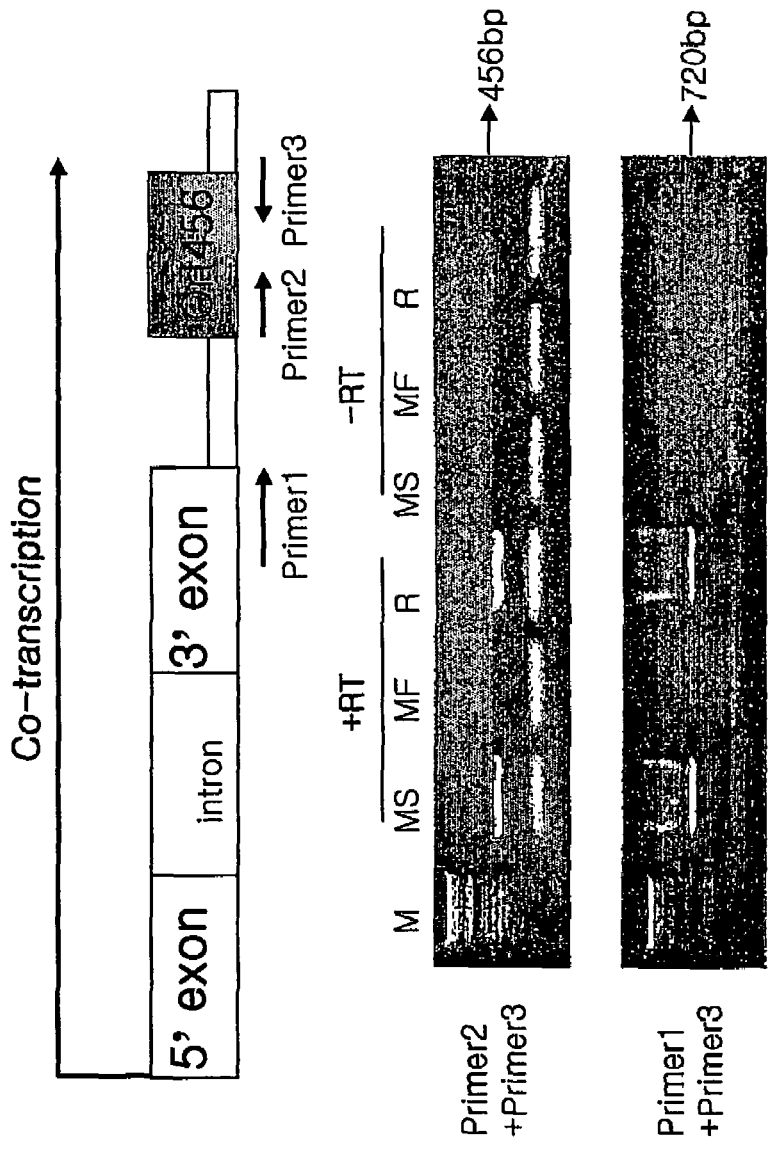
FIG. 8 shows the results of Northern-blot analysis on mtRNAs of fertile, sterile, and restored lines with the orf456 probe. About 15 μg/lane of RNA is loaded in 1.2% agarose gel and is transferred to a $N^+$ nylon membrane. F: fertile line, S: sterile line, R: restorer line.

FIG. 7 shows the results of RT-PCR experiments on the orf456 gene which is located on the 3' region of the coxII gene in the sterile line. The RT-PCR with the primer pair (SEQ ID NOs: 9 and 10) is performed to detect the fact that the newly-made orf456 is really and uniquely transcribed in the sterile line. The RT-PCR with the primer set (SEQ ID NOs:6 and 10) is performed to detect whether the orf456 gene is co-transcribed with coxII located on the upstream region. FIG. 8 shows the results of Northern-blot analysis on mtRNAs of fertile, sterile, and restored lines with the orf456 probe. About 15 μg/lane of RNA was loaded in 1.2% of agarose gel and transferred to a N+ nylon membrane. F: fertile line, S: sterile line, R: restorer line. FIG. 3 shows the results of Northern-blot analysis on mtRNAs of fertile, sterile, and restorer lines with the orf456 probe. The orf456 open reading frame is really and uniquely transcribed in the sterile and restorer line carrying S-cytoplasm.

Example 4

Bacterial Growth Inhibition Test

To investigate how orf456 affects plant mitochondria and results in mitochondrial dysfunction and male sterility, a heterologous systems, i.e. a bacterial cell, was adopted. The possible toxicity on a bacterial cell of the orf456 gene was examined.

Figure 9:
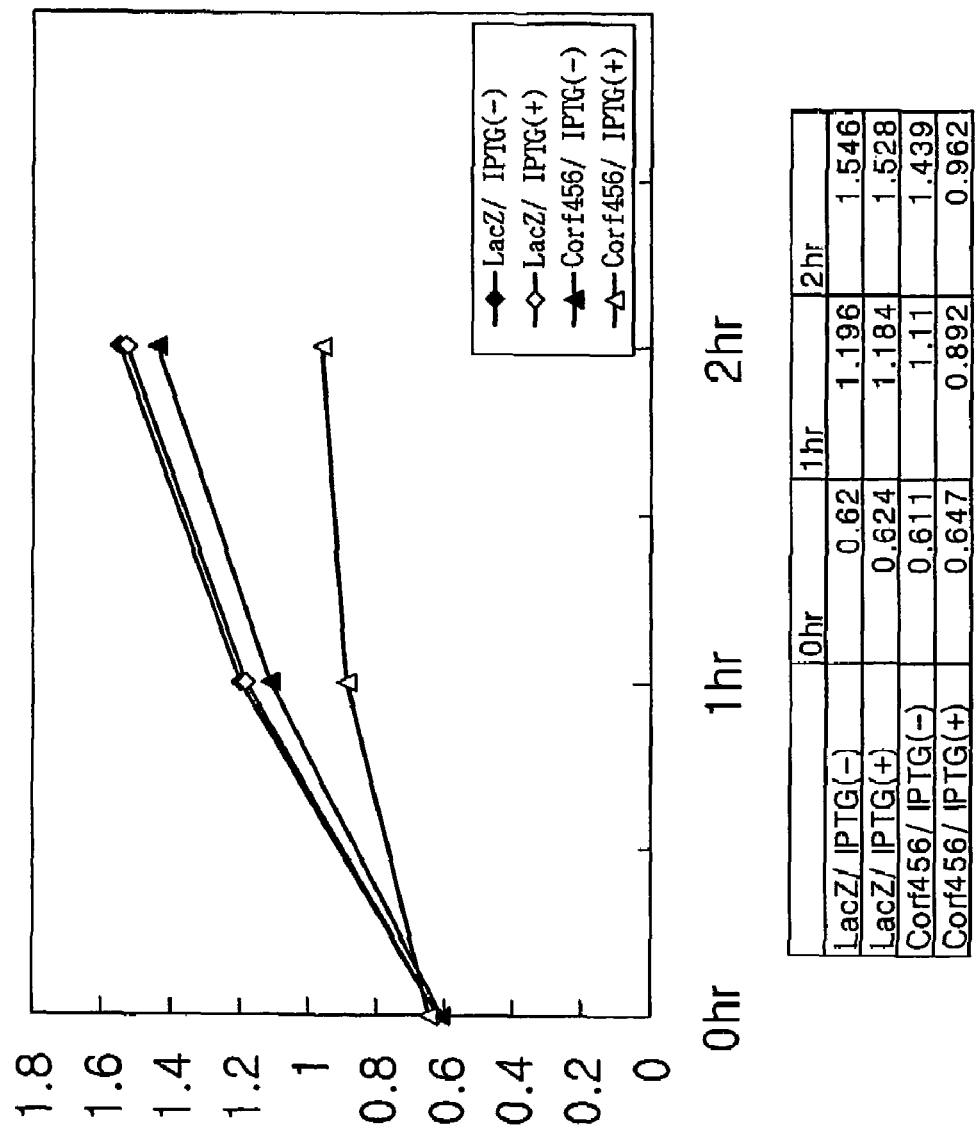
FIG. 9 shows the results of bacterial growth inhibition tests by orf456 gene expression.

The orf456 gene was cloned into a pTrcHis2-TOPO expression vector and transfected into an *E. coli* strain Top10 cell (Invitrogen, USA). As controls, cells carrying pTrcHis2-TOPO+LacZ genes were cultured under the same conditions and induced by 1 mM IPTG. Cloning and transformation were conducted according to the manufacturers protocols. Top10 cells containing the LacZ gene (control) and orf456 gene were precultured in 3 ml of LB medium with 50 μg/ml of ampicillin at 37° C. for 16 hrs. 50 μl of a primary culture was transferred to 20 ml of the medium and cultured at 37° C. for 2-3 hrs. At the time of O.D.$_{600}$=0.6, 1 mM of IPTG was added and the growth rate of each transformant was monitored by its absorbance every hour. The growth of *E. coli* cells was dramatically impaired as soon as expression of orf456 was induced. FIG. 9 shows the results of bacterial growth inhibition tests by orf456 gene expression. The growth rate of *E. coli* carrying constructs with orf456 and induced by 1 mM IPTG is severely impaired compared to other constructs.

Example 5

Test for Targeting Foreign Gene to Mitochondria and Transformants Preparation 5-1. Constructs Preparation for *Arabidopsis* Transformation The egfp-1 fragment (SE ID NO: 4, GFP variants purchased from Clontech) were amplified from the pEGFP-1 vector (Clontech, Palo Alto, USA). The amplified coxIV target sequences (SEQ ID NO:3, Yeast DNA fragment for cytochrome c oxidase subunit IV precursor) and egfp-1 gene were ligated by T4 DNA ligase (Promega, USA), then cloned to the pCAMBIA2300 vector (MJC). Also, a coxIV-orf456 construct and nontargeting-orf456 construct as shown in FIG. 9 were prepared and ligated into the pCAMBIA2300 vector.

Figure 10:
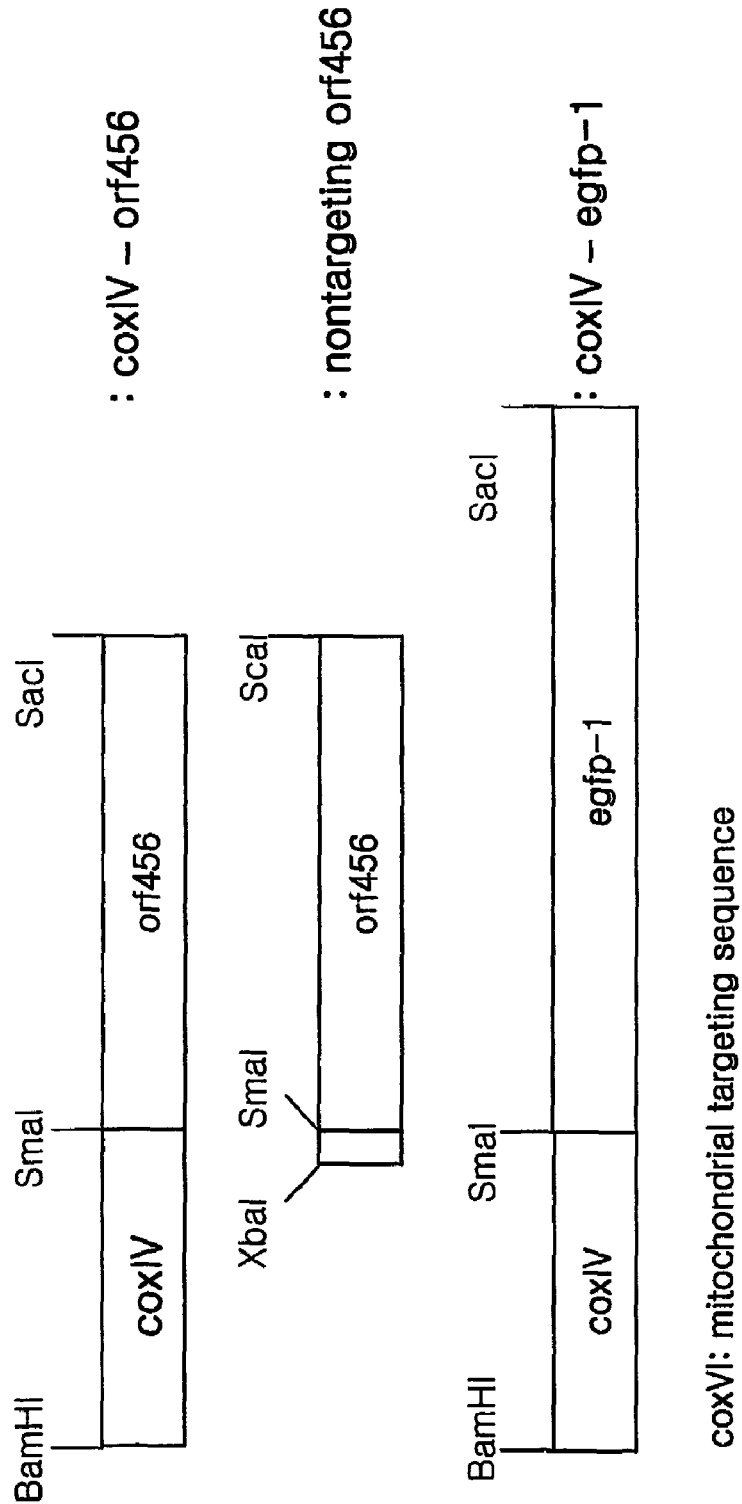
FIG. 10 shows the construction of orf456 and egfp-1 transgenes for transformation. The diagram shows the strategy for cloning each gene construct into the pCAMBIA2300 plant transformation vector.

In FIG. 10, the nopaline synthase (nos) gene terminator sequence was fused to the 3' end of the orf456 and egfp-1 sequences. In the first construct (referred to as coxIV-orf456), the orf456 sequence was fused to the transit peptide sequence of the presequences of the nuclear coxIV gene of yeast strain Y187, (Stratagene, USA). The second construct (referred to as nontargeting-orf456) did not have the mitochondrial targeting peptide sequences. The third construct (referred to as coxIV-egfp-1) was made using coxIV presequences and egfp-1 from pEGFP-1 vector (Clontech, USA).

5-2. Onion Transient Expression Experiments

The fusion constructs (coxIV presequence fused to egfp-1 gene) in the pCAMBIA2300 vector were transiently expressed in onion epidermal cells after transfection. Inner epidermal peels (2×2 cm) of onion were placed on agar plates containing 1×MS salts, 30 g/L sucrose, and 2% agar, pH 5.7. Peels were bombarded within 1 h of transfer to agar plates. Particle bombardments were done as described by Scott et al (1999). After incubation of 20-22 hrs in light, Mitochondrial localization was examined by confocal laser scanning microscopy using the Radiance 2000 Multi-Photon Imaging System (Bio-Rad, Hercules, Calif.) at the National Instrumentation Center for Environmental Management (NICEM, Suweon, South Korea).

Figure 11:
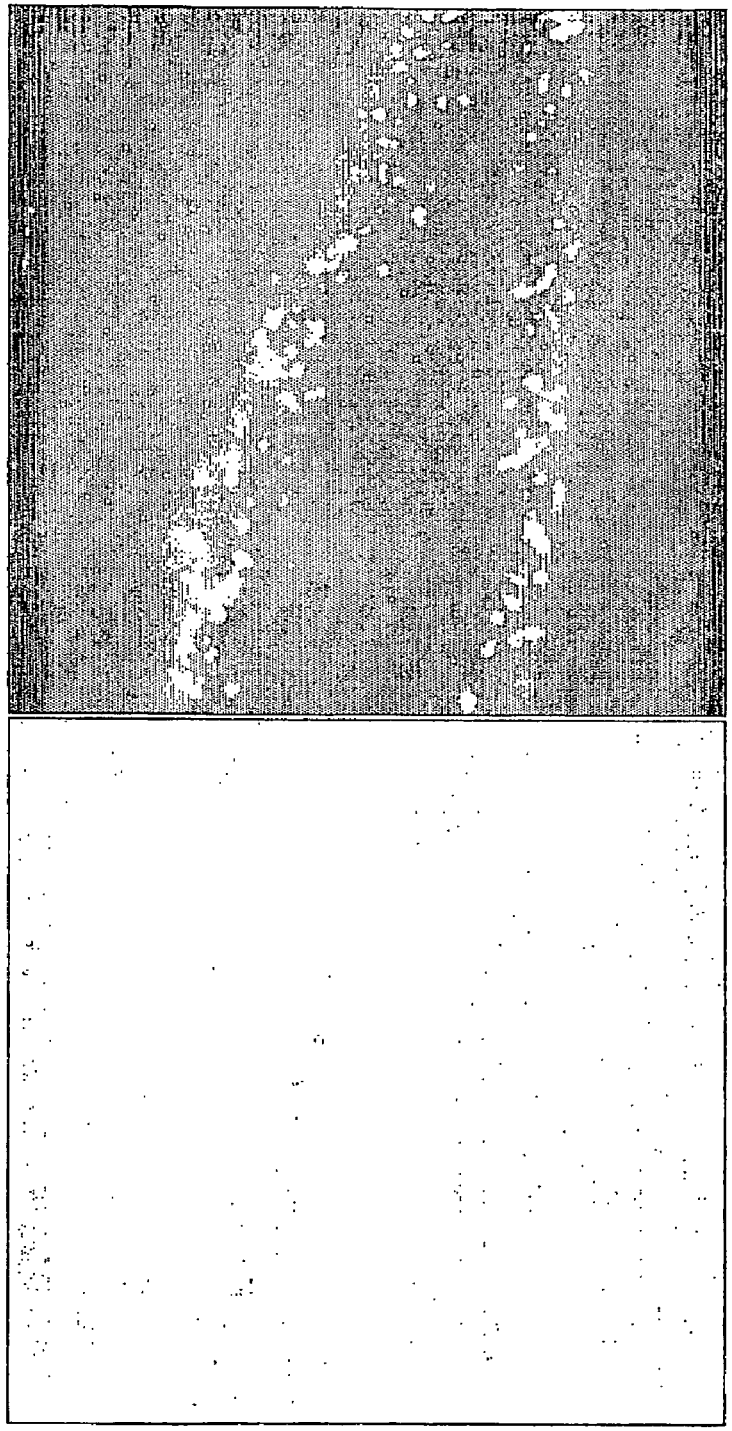
FIG. 11 shows an image of GFP fluorescence in an onion transient expression assay.

FIG. 11 shows an image of GFP fluorescences in the onion transient expression assay. The left picture shows the GFP fluorescences in the onion by coxIV+egfp-1 construct. Mitotracker CMSRox dye (Molecular Probe Co., USA) was used for detection of mitochondria (right picture). The GFP image and Mitotracker dye images completely matched.

5-3. *Arabidopsis* Plant Transformation

The *Arabidopsis thaliana* ecotype Columbia plants were used for transformation experiments. A strong CaMV 35S promoter and nos terminator were used in vector construction. The mitochondrial target sequence used was derived from the Yeast coxIV presequences, and the orf456 and egfp-1 sequences used in the constructions were amplified by PCR to facilitate cloning. Inserts were confirmed by enzyme digestion and sequencing. The inserts were digested with an appropriate restriction enzyme to clone into the plant transformation vector pCAMBIA2300. Clones which had correct inserts were selected on the kanamycin LB medium. Transformations into *Agrobacterium tumefaciens* LBA4404 were done by the heat-shock method (Sambrook et al., 1989). The *Arabidopsis thaliana* plants were transformed by *Agrobacterium tumefaciens* carrying the coxIV (targeted)-orf456 and non-targeted orf456 constructs. The *Agrobacterium tumefaciens*-mediated transformation was performed by a modified floral-dip method (Clough and Bent, 1998). Transgenic plants were selected on a medium containing kanamycin sulfate (50 μg ml$^{-1}$). Green plants surviving the antibiotic treatment were retained for further analyses.

Figure 12:
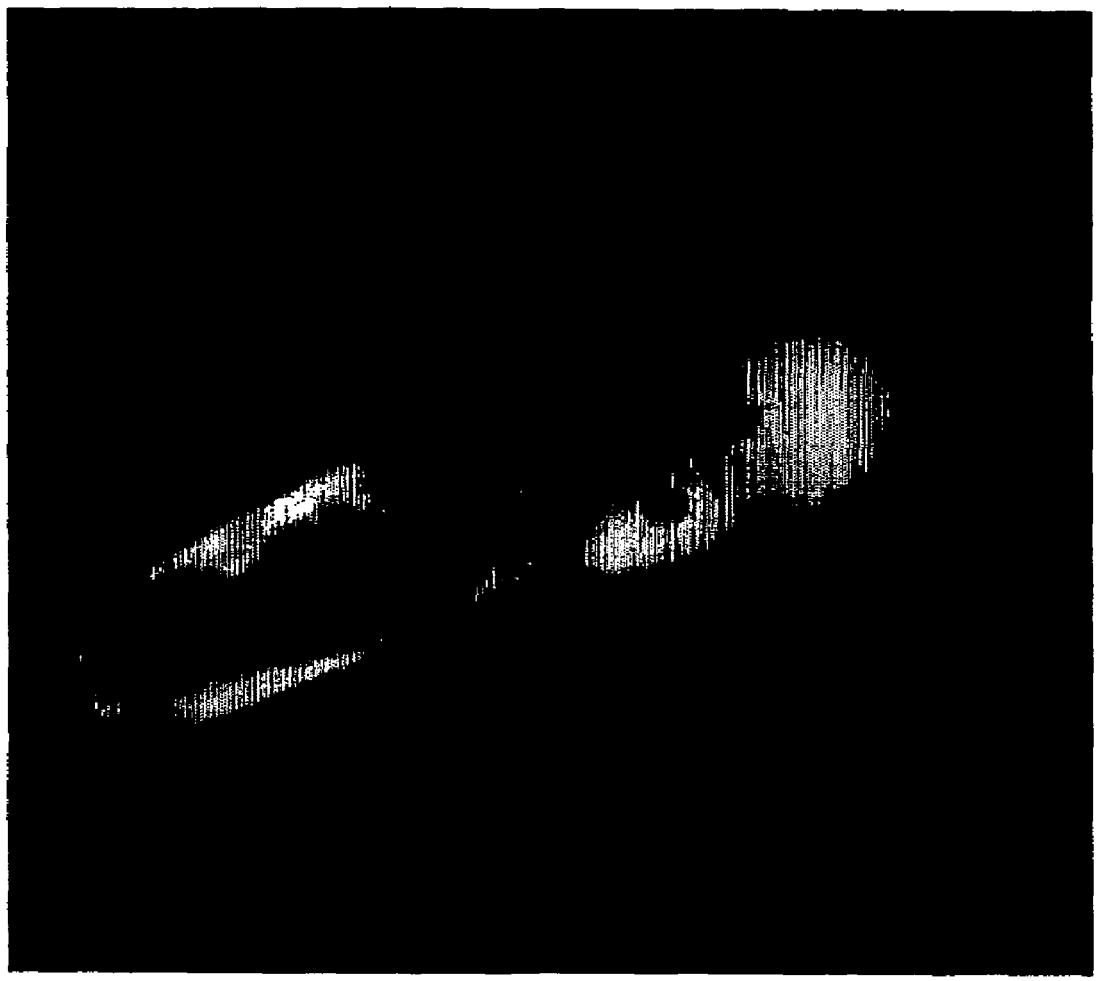
FIG. 12 shows an image of GFP fluorescence in an *Arabidopsis* transformant.

FIG. 12 shows an image of GFP fluorescences expressed in roots of *Arabidopsis thaliana*.

The vegetative growth of transformants was uniform and similar to that of non-transformed control plants or non-targeted transformants. At flowering, the 31 plants out of 51 *Arabidopsis* transformants transfected with mitochondrial targeting signal showed male-sterile phenotype in the $T_1$ generation. This classification was based on flower morphology and seed set. The 3 *Arabidopsis* plants out of 50 transformants transfected with non-targeted constructs showed male-sterile phenotype. This was a rather unexpected result in the case of non-targeting experiments. However, it was postulated that this orf456 product in the cytoplasm could not have any deleterious effect in plant cells as the results proven at the bacterial growth inhibition tests even if it did not express in the mitochondria.

Figure 13:
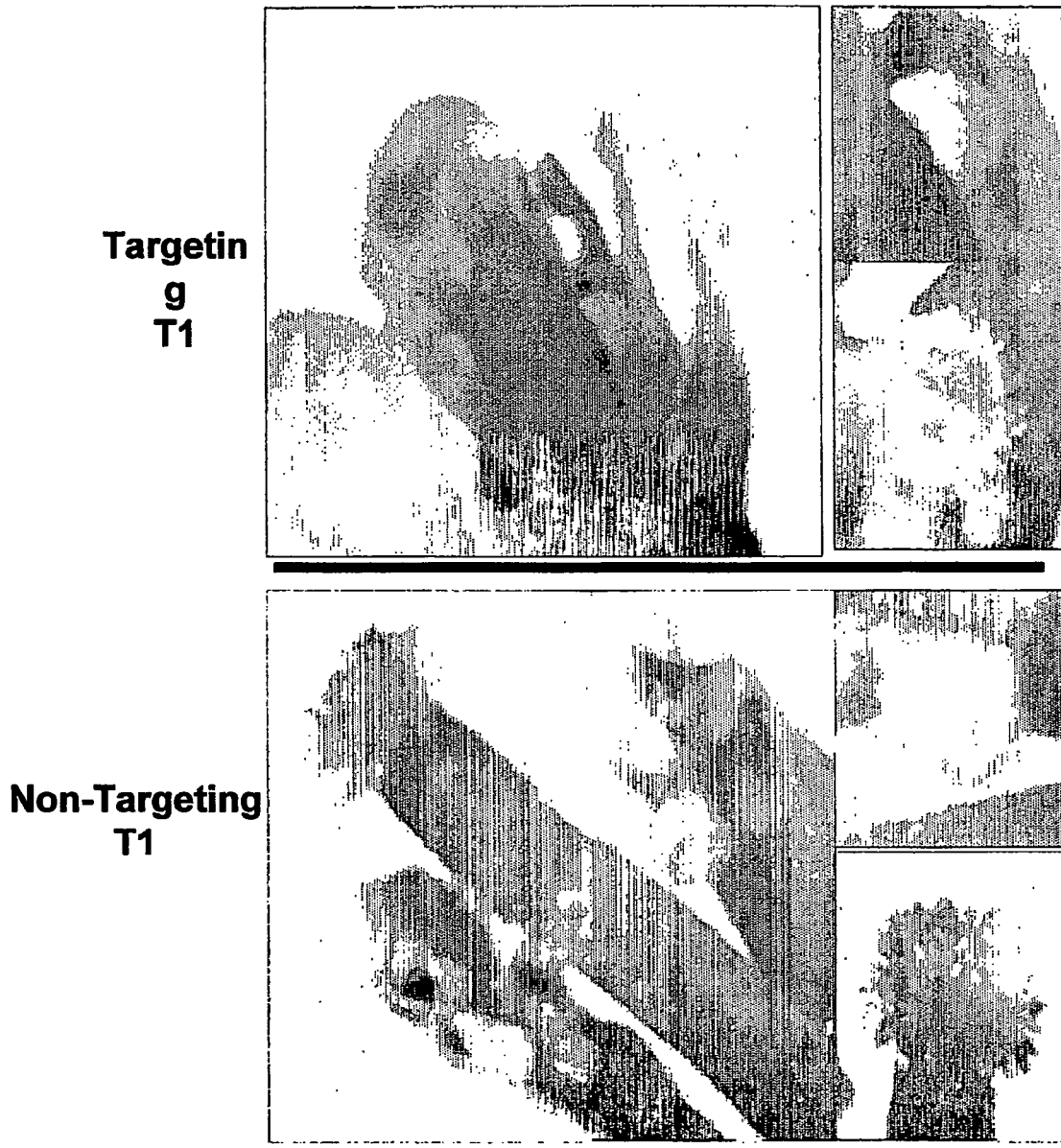
FIG. 13 shows flower morphology of the male sterile (mitochondria-targeted, a) transformants and male fertile (mitochondria-non-targeted, b) transformants.

FIG. 13 shows flower morphology of the male sterile (mitochondria-targeted) transformants and male fertile (mitochondria-non-targeted) transformants. "a" is a floral picture of male sterile transformants carrying mitochondria-targeted orf456, and "b" is a floral picture of male fertile transformants carrying mitochondria-non-targeted orf456.

Figure 14:
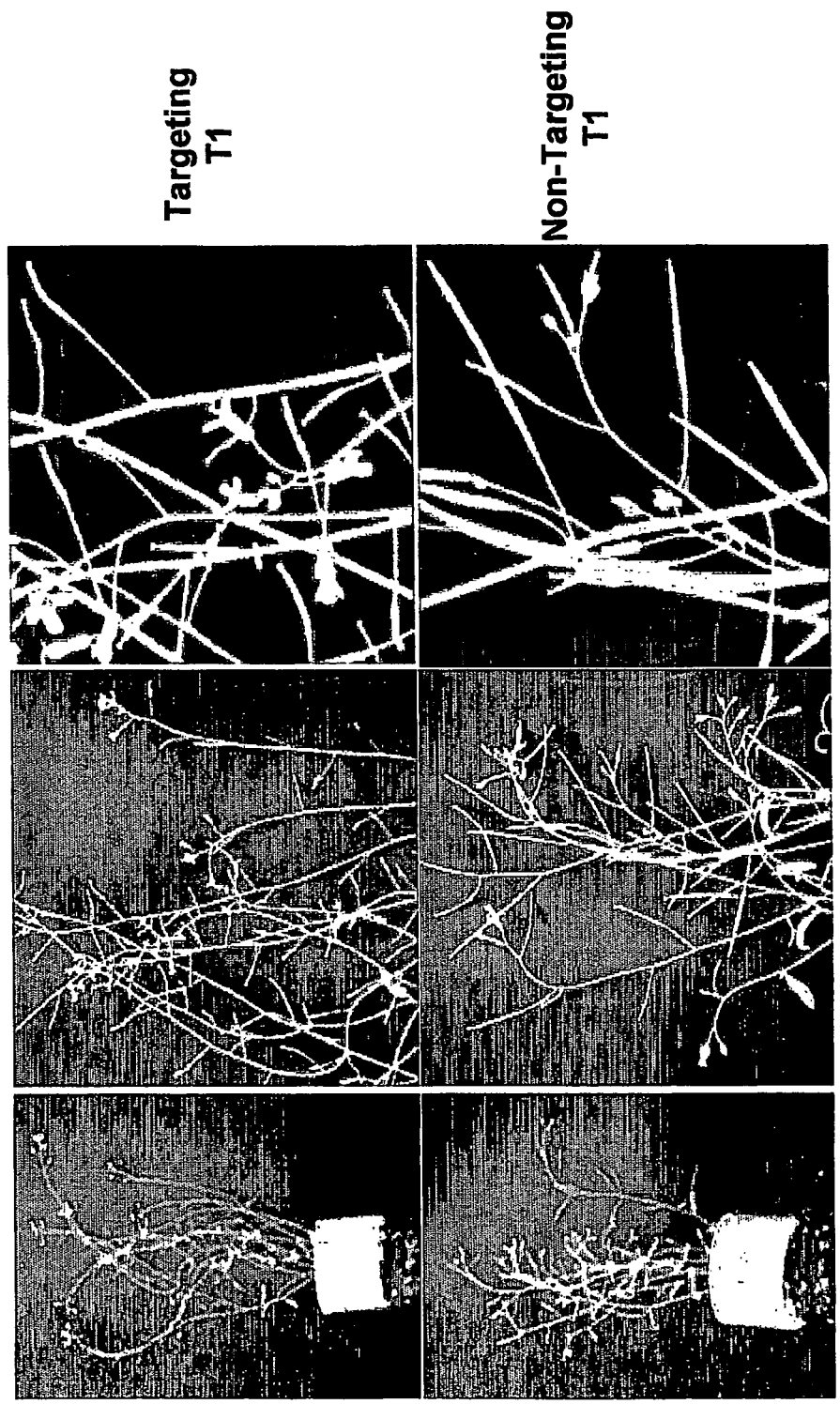
FIG. 14 shows a transgenic *Arabidopsis* phenotype at the stage of seed sets in the mitochondrial-targeted transformants.

FIG. 14 shows an *Arabidopsis* phenotype at the stage of seed sets in the mitochondrial-targeted transformants (a) and in the mitochondrial-non-targeted transformants (b).

Figure 15:
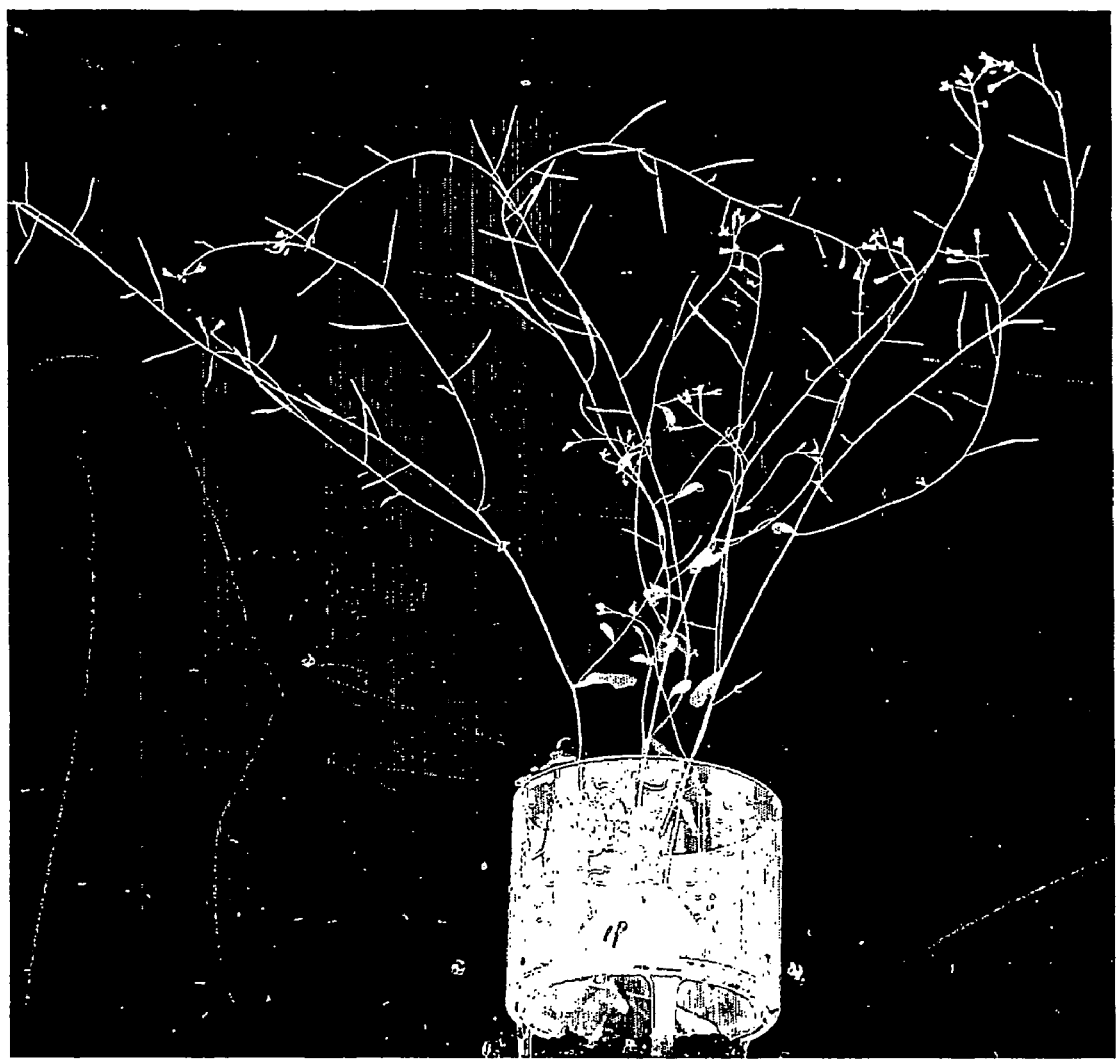
FIG. 15 shows heterogenic $T_0$ transgenic *Arabidopsis* transformants which show both the male sterile and male fertile phenotypes.

FIG. 15 is a picture of *Arabidopsis* transformants which shows the male sterile and male fertile phenotypes in the same stocks, which come from the vacuum infiltration transformation methods. The arrow indicates the normal silique produced from normal pollination, and the arrowhead indicates the flower which is not pollinated and did not produce normal seed sets.

5-4. Confirmation of Transgenic Plants

Total leaf DNA for PCR and Southern-blot analysis was extracted (Kim et al., 2001). PCR amplification was performed on 100 ng of total DNA with a thermal cycler PTC-200 (MJ Research, USA) using thirty cycles of 30 s at 94° C., 45 s at 55° C., and 90 s at 72° C. The total DNA digested with restriction enzymes were electrophoresed on a 0.8% agarose gel, transferred onto a nylon membrane, and hybridized with [$\alpha$-$^{32}$P] dCTP (Amersham Pharmacia Biotech, NJ, USA)-labeled probes.

Table 2 shows the male fertility evaluation based on pollen production in transgenic $T_1$ *Arabidopsis* plants confirmed to contain the orf456 transgene.

TABLE 2

| Plant type | No. of plants | Classification | |
|---|---|---|---|
| | | Fertile | Sterile |
| Non-targeting | 50 | 47 | 3 |
| Targeting | 51 | 20 | 31 |

Example 6

Determination of Male Fertile or Sterile by Genotyping 6-1. Primer

The specific oligonucleotide primers that can be used in a PCR assay to distinguish maintainer (N-cytoplasm) and CMS (S-cytoplasm) lines of chili pepper (*Capsicum annuum* L.) are designed.

coxII SCAR PCR Primer

Forward primer (SEQ ID No:15)—a part of coding region of coxII gene

Reverse primer (SEQ ID No:16)—a part of the sequence that is unique to the CMS lines.

apt6 SCAR PCR Primer

Forward primer (SEQ ID No: 17)—a part of coding region of atp6 gene

Reverse primer (SEQ ID No:18)—a part of the sequence that is unique to the CMS lines.

coxII Positive Control

Forward primer: SEQ ID NO: 19

Reverse primer: SEQ ID NO: 20

6-2. PCR Assay for Distinguishing CMS and Maintainer Lines in Chili Pepper

Using the primer sets, PCR was performed as described below.

Total DNA (200 ng) was mixed with 200 µmol of dNTP, 20 pM of each primer, 5 µl of 10× reaction buffer, and 2.5 unit of Taq polymerase (Takara, Japan) in a 50 µl reaction volume. PCR amplification for atp6 SCAR marker was carried out at 94° C. (1 min), 52° C. (1 min), and 72° C. (2 min), for 35 cycles. Amplified DNA was electrophoresed in 0.8% agarose gel. In the case of coxII SCAR marker, annealing was performed at 56° C.

Figure 16:
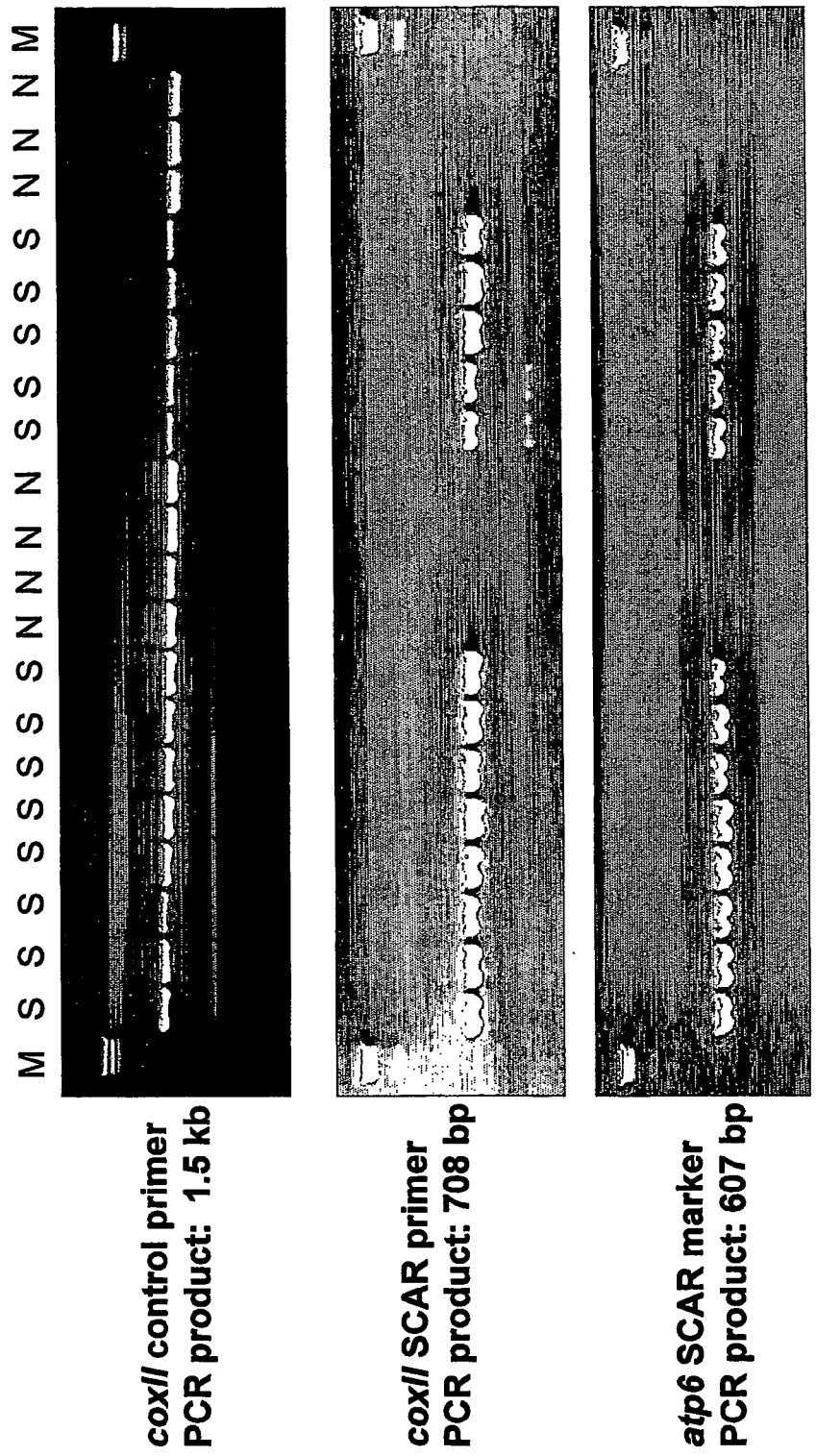
FIG. 16 shows a PCR Amplification of 20 pepper cultivars or accessions with CMS-specific SCAR primer pairs.

FIG. 16 is a picture showing PCR results for the 20 pepper cultivars, where "N" indicates a fertile phenotype, "S" indicates a sterile phenotype, and "M" indicates a λ/HindIII DNA marker.

Using the coxII SCAR primer pair, there was an amplification of a 708 bp DNA fragment in the CMS lines, but no PCR amplification was observed in the maintainer lines. In case of the atp6 SCAR primer pair, there was an amplification of a 607 bp DNA fragment in the CMS lines, but no PCR amplification was observed in the maintainer lines. To check whether PCR reactions were done well, a PCR primer pair spanning the coding region of the coxII gene was used as a control. The fragment size of PCR amplification was about 1.5 kb. The *Capsicum annuum* used in the PCR experiment is listed in Table 1.

TABLE 1

| | Cultivar or Accession | Cytoplasmic Genotype* | Phenotype |
|---|---|---|---|
| 1 | 80-2 | S | Sterile |
| 2 | 80-5 | S | Sterile |
| 3 | KC268-1-1 | S | Sterile |
| 4 | KC268-1-3 | S | Sterile |
| 5 | KC268-2-1 | S | Sterile |
| 6 | CMS-A | S | Sterile |
| 7 | Chilsungcho-A | S | Sterile |
| 8 | Milyang-A | S | Sterile |
| 9 | CMS-B | N | Fertile |
| 10 | Chilsungcho-1 | N | Fertile |
| 11 | Subicho-1 | N | Fertile |
| 12 | Milyang-B | N | Fertile |
| 13 | FC-2(CMS from China) | S | Sterile |
| 14 | FC-3(CMS from Europe) | S | Sterile |
| 15 | FC-4 | S | Sterile |
| 16 | 4570 | S | Sterile |
| 17 | 4578 | S | Sterile |
| 18 | TF68 | N | Fertile |
| 19 | Ancho | N | Fertile |
| 20 | CM334 | N | Fertile |

*N: N-cytoplasm, S: S-cytoplasm

What is claimed is:

1. An isolated DNA fragment specific to a cytoplasmic male sterile pepper comprising a polynucleotide consisting of the 456-nucleotides from the $223^{rd}$ to the $678^{th}$ of SEQ ID NO:1.

2. The DNA fragment according to claim 1, wherein the DNA fragment comprises a polynucleotide which comprises SEQ ID NO:1.

3. The DNA fragment according to claim 1, wherein the polynucleotide is located at the 3'-terminal of a coxll gene.

4. A transgenic male sterile plant comprising a polynucleotide consisting of the 456-nucleotides from the $223^{rd}$ to the $678^{th}$ nucleotides of SEQ ID NO:1.

5. A construct for use in obtaining a transgenic male sterile plant, comprising:
   a) a polynucleotide consisting of the 456-nucleotides from the $223^{rd}$ to the $678^{th}$ nucleotides of SEQ ID NO:1;
   b) a promoter that is active in the plant, and operably linked to the polynucleotide so as to achieve expression thereof and
   c) a DNA sequence capable of transferring a protein expressed by the polynucleotide of a) to the mitochondrion.

6. The construct according to claim 5, wherein the DNA sequence of part (c) comprises the nucleotide sequence of SEQ ID NO. 3.

7. The construct according to claim 5, wherein the plant is one or more selected from the group consisting of Solanaceae plant species; Brassicaceae plant species; floral plant species; and woody plants.

8. A method for producing male sterile transgenic plants, comprising transforming the construct of claim 5 into plants or plant.

9. The method according to claim 8, wherein the plant is one or more selected from the group consisting of Solanaceae plant species; Brassicaceae plant species; floral plant species; and woody plants.

10. A method for inhibiting the production of pollen in plants, comprising transforming the construct of claim 5 into plants or plant cells, wherein a transgenic plant is regenerated from the transformed plant cells.

11. The method according to claim 10, wherein the plant is one or more selected from the group consisting of Solanaceae plant species; Brassicaceae plant species; floral plant species; and woody plants.

12. The transgenic male sterile plant according to claim 4, wherein the plant is one or more selected from the group consisting of chili pepper, eggplant, tobacco, tomato, petunia, turnip, cauliflower, broccoli, lily and chrysanthemum.

* * * * *

UNITED STATES PATENT AND TRADEMARK OFFICE
CERTIFICATE OF CORRECTION

| | |
|---|---|
| PATENT NO. | : 7,728,194 B2 |
| APPLICATION NO. | : 10/555824 |
| DATED | : June 1, 2010 |
| INVENTOR(S) | : Kim et al. |

It is certified that error appears in the above-identified patent and that said Letters Patent is hereby corrected as shown below:

Column 1,
Line 11, "PCT/KR03/100904" should read --PCT/KR03/00904--.

Column 23,
Line 21, "to the 678$^{th}$ of SEQ ID" should read --to the 678$^{th}$ nucleotides of SEQ ID--.

Column 24,
Line 24, after "plant" insert --cells, wherein a transgenic plant is regenerated from the transformed plant cells--.

Signed and Sealed this
Eighteenth Day of January, 2011

David J. Kappos
*Director of the United States Patent and Trademark Office*